(12) United States Patent
Mu et al.

(10) Patent No.: US 7,973,055 B2
(45) Date of Patent: *Jul. 5, 2011

(54) CRYSTALLINE FORMS OF A BIPHENYL COMPOUND

(75) Inventors: YongQi Mu, Los Altos, CA (US); Yu-Hua Ji, Redwood City, CA (US); Leticia Maria Preza, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 1153 days.

This patent is subject to a terminal disclaimer.

(21) Appl. No.: 11/715,569

(22) Filed: Mar. 8, 2007

(65) Prior Publication Data

US 2008/0058374 A1    Mar. 6, 2008

Related U.S. Application Data

(60) Provisional application No. 60/780,652, filed on Mar. 9, 2006.

(51) Int. Cl.
  *A61K 31/445* (2006.01)
  *C07D 211/06* (2006.01)
(52) U.S. Cl. ........................... 514/317; 546/226
(58) Field of Classification Search .................. 514/317; 546/226
  See application file for complete search history.

(56) References Cited

U.S. PATENT DOCUMENTS

| | | | |
|---|---|---|---|
| 3,903,137 A | 9/1975 | Miura et al. | |
| 6,635,764 B2 | 10/2003 | Mammen et al. | |
| 6,693,202 B1 | 2/2004 | Aggen et al. | |
| 7,141,671 B2 * | 11/2006 | Mammen et al. | 546/224 |
| 7,687,519 B2 * | 3/2010 | Mu et al. | 514/317 |
| 2003/0018019 A1 | 1/2003 | Meade et al. | |
| 2005/0113413 A1 | 5/2005 | Wilson et al. | |
| 2005/0277688 A1 | 12/2005 | Li et al. | |
| 2006/0205778 A1 | 9/2006 | Mu et al. | |
| 2006/0205949 A1 | 9/2006 | Dalziel et al. | |
| 2008/0058374 A1 * | 3/2008 | Mu et al. | 514/317 |

FOREIGN PATENT DOCUMENTS

EP   0 747 355 A1   12/1996
WO   WO 2006/099165   9/2006

OTHER PUBLICATIONS

Seddon "peudopolymorph . . . " Crystal growth and design v.4, p. 1087 (2004) (two pages from internet).*
Braga et al. "Making crystal . . . " Royal soc. chemistry. chem. com,mun. p. 3635-3645 (2005).*
Dean "Analytical chemistry handbook" p. 10.24-10.26 (1993).*

(Continued)

*Primary Examiner* — Celia Chang
(74) *Attorney, Agent, or Firm* — Jeffrey A. Hagenah; Shelley Eberle

(57) ABSTRACT

The invention provides crystalline forms of biphenyl-2-ylcarbamic acid 1-[2-({3-[2-(4-hydroxybenzylamino)ethylcarbamoyl]benzoyl}methylamino)ethyl]piperidin-4-yl ester, and pharmaceutically acceptable solvates thereof. The crystalline form can be a freebase (Form I or II), a salt such as a hemiedisylate salt or a heminapadisylate salt, or a solvate of a salt such as a heminapadisylate methanolate or a heminapadisylate ethanolate. The invention also provides pharmaceutical compositions comprising these crystalline compounds or prepared using these compounds; processes and intermediates for preparing the crystalline compounds; and methods of using these compounds to treat a pulmonary disorder.

5 Claims, 20 Drawing Sheets

OTHER PUBLICATIONS

Berstein "Polymorphism in molecular crystals" p. 115-118, 272 (2002).*

Drugs of the Future, 7(4), pp. 227-228 (1982).

Naito et al., "Selective Muscarinic Antagonist. II.[1] Synthesis and Antimuscarinic Properties of Biphenylylcarbamate Derivatives", Chem. Pharm. Bull., vol. 46, No. 8, pp. 1286-1294 (1998).

* cited by examiner

CRYSTALLINE FORMS OF A BIPHENYL COMPOUND

CROSS-REFERENCE TO RELATED APPLICATIONS

This application claims the benefit of U.S. Provisional Application No. 60/780,652, filed on Mar. 9, 2006; the entire disclosure of which is incorporated herein by reference.

BACKGROUND OF THE INVENTION

1. Field of the Invention

The present invention relates to novel crystalline forms of a biphenyl compound and solvates thereof, which are expected to be useful for treating pulmonary disorders. The invention also relates to pharmaceutical compositions comprising the crystalline compounds or prepared from such compounds, processes and intermediates for preparing the crystalline compounds and methods of using such compounds to treat pulmonary disorders.

2. State of the Art

Commonly-assigned U.S. Provisional Application No. 60/660,435 filed on Mar. 10, 2005, and U.S. patent application Ser. No. 11/371,803 filed on Mar. 9, 2006, both entitled "Biphenyl Compounds Useful As Muscarinic Receptor Antagonists", discloses novel biphenyl compounds that are expected to be useful for treating pulmonary disorders such as chronic obstructive pulmonary disease (COPD) and asthma. In particular, the compound biphenyl-2-ylcarbamic acid 1-[2-({3-[2-(4-hydroxybenzylamino)ethylcarbamoyl]benzoyl}methylamino)ethyl]piperidin-4-yl ester is specifically disclosed in this application as possessing muscarinic receptor antagonist activity.

The chemical structure of biphenyl-2-ylcarbamic acid 1-[2-({3-[2-(4-hydroxybenzylamino)ethylcarbamoyl]benzoyl}methylamino)ethyl]piperidin-4-yl ester is represented by formula I:

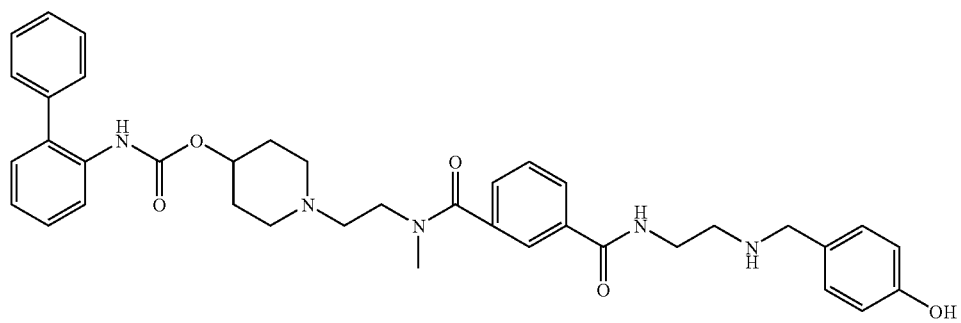

I

The compound of formula I has been named using the commercially-available AutoNom software (MDL, San Leandro, Calif.).

Therapeutic agents useful for treating pulmonary or respiratory disorders are advantageously administered directly into the respiratory tract by inhalation. In this regard, several types of pharmaceutical inhalation devices have been developed for administering therapeutic agents by inhalation including dry powder inhalers (DPI), metered-dose inhalers (MDI) and nebulizer inhalers. When preparing pharmaceutical compositions and formulations for use in such devices, it is highly desirable to have a crystalline form of the therapeutic agent that is neither hygroscopic nor deliquescent and which has a relatively high melting point (typically greater than about 150° C.) thereby allowing the material to be micronized without significant decomposition or loss of crystallinity.

No crystalline forms of the compound of formula I have been reported previously. Accordingly, a need exists for stable, non-deliquescent crystalline forms of the compound of formula I which have acceptable levels of hygroscopicity and relatively high melting points.

SUMMARY OF THE INVENTION

The present invention provides crystalline forms of biphenyl-2-ylcarbamic acid 1-[2-({3-[2-(4-hydroxybenzylamino)ethylcarbamoyl]benzoyl}methylamino)ethyl]piperidin-4-yl ester (formula I). The crystalline form may be a pharmaceutically acceptable salt, a pharmaceutically acceptable solvate of such a salt, or a freebase. For example the present invention provides the crystalline compound as a hemiedisylate salt, a heminapadisylate methanolate, a heminapadisylate ethanolate, a heminapadisylate salt, or a freebase (Form I or II).

Surprisingly, the crystalline forms of the invention have been found not to be deliquescent, even when exposed to up to 90% relative humidity. Additionally, the crystalline forms have acceptable levels of hygroscopicity and most have relatively high melting points, greater than about 150° C. For example, the crystalline hemiedisylate salt has a melting point around 151° C., and the crystalline heminapadisylate salt has a melting point around 160° C.

Among other uses, crystalline forms of the compound of formula I are useful for preparing pharmaceutical compositions expected to have utility for treating pulmonary disorders. Accordingly, one aspect of the invention pertains to a pharmaceutical composition comprising a pharmaceutically acceptable carrier and a therapeutically effective amount of a crystalline form of the compound of formula I.

Yet another aspect of the invention pertains to compositions comprising a crystalline form of the compound of formula I in combination with one or more other therapeutic agents. Accordingly, in one embodiment, the invention is directed to a composition comprising (a) a pharmaceutically acceptable carrier and a therapeutically effective amount of a crystalline form of the compound of formula I; and (b) a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the crystalline form and the agent are formulated together or separately. When the agent is formulated separately, a pharmaceutically acceptable carrier may be included.

Another aspect of the invention relates to a pharmaceutical composition comprising an aqueous isotonic saline solution comprising a crystalline form of the compound of formula I, wherein the solution has a pH in the range of from about 4 to 6.

In one embodiment, the invention provides a drug delivery device comprising a dry powder inhaler containing a pharmaceutical composition comprising a pharmaceutically acceptable carrier and a crystalline form of the compound of formula I.

The compound of formula I has muscarinic receptor antagonist activity. Accordingly, crystalline forms of formula I or a pharmaceutically acceptable solvate
thereof, is useful for treating pulmonary disorders such as asthma and chronic obstructive pulmonary disease. Thus, another aspect of the invention pertains to a method for treating a pulmonary disorder comprising administering to a patient a therapeutically effective amount of a crystalline form of the compound of formula I. Still another aspect of the invention relates to a method of producing bronchodilation in a patient comprising administering to the patient a bronchodilation-producing amount of a crystalline form of the compound of formula I. In one embodiment, the compound is administered by inhalation. The invention also provides a method of treating chronic obstructive pulmonary disease or asthma comprising administering to a patient a therapeutically effective amount of a crystalline form of the compound of formula I. Another aspect of the invention is directed to a method for antagonizing a muscarinic receptor in a mammal comprising administering to the mammal a therapeutically effective amount of a crystalline form of the compound of formula I.

The invention is directed to processes for preparing crystalline forms of the compound of formula I. The invention also provides a process for purifying and isolating the compound of formula I comprising forming a crystalline salt, solvate or freebase of biphenyl-2-ylcarbamic acid 1-[2-({3-[2-(4-hydroxybenzylamino)ethylcarbamoyl]benzoyl}methylamino)ethyl]piperidin-4-yl ester. The invention is further directed to products prepared by the processes described herein.

The invention is also directed to a crystalline form of the compound of formula I in a micronized form; and to pharmaceutical compositions comprising a pharmaceutically acceptable carrier and a micronized crystalline form of the compound of formula I.

The invention is also directed to a crystalline form of the compound of formula I for use in therapy or as a medicament. Additionally, the invention relates to the use of crystalline forms of the compound of formula I for the manufacture of a medicament; especially for the manufacture of a medicament for the treatment of a pulmonary disorder or for antagonizing a muscarinic receptor in a mammal.

BRIEF DESCRIPTION OF THE DRAWINGS

Various aspects of the present invention are illustrated by reference to the accompanying drawings.

FIG. 5C, top line). The crystalline heminapadisylate methanolate is further characterized by the DSC traces shown in FIG. 6A and the TGA shown trace in FIG. 7.

DETAILED DESCRIPTION OF THE INVENTION

Figure 1:
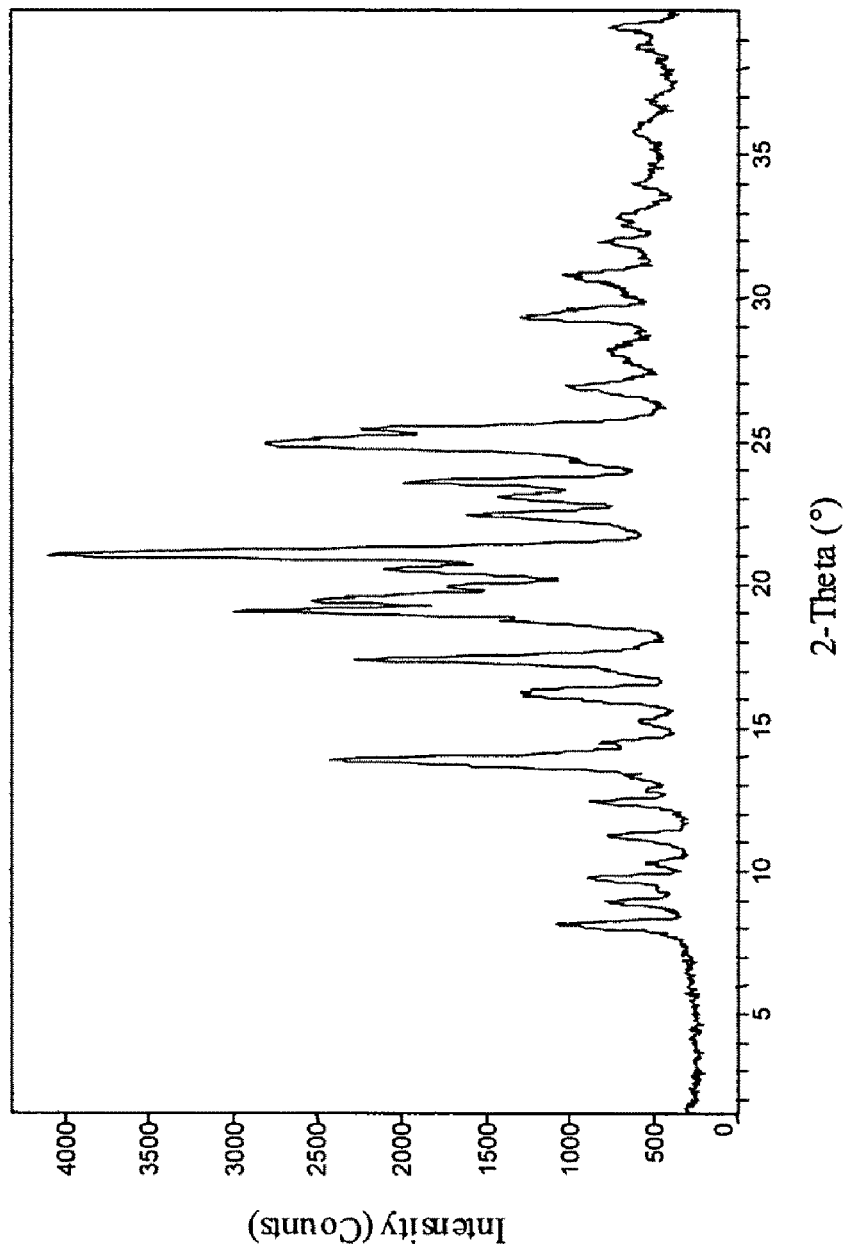
FIG. 1 shows a powder x-ray diffraction (PXRD) pattern of a crystalline hemiedisylate salt of biphenyl-2-ylcarbamic acid 1-[2-({3-[2-(4-hydroxybenzylamino)ethylcarbamoyl]benzoyl}methylamino)ethyl]piperidin-4-yl ester (the compound of formula I).

The invention provides crystalline forms of biphenyl-2-ylcarbamic acid 1-[2-({3-[2-(4-hydroxybenzylamino)ethylcarbamoyl]benzoyl}methylamino)ethyl]piperidin-4-yl ester. The crystalline form may be a pharmaceutically acceptable salt such as a hemiedisylate salt or a heminapadisylate salt, a pharmaceutically acceptable solvate of such a salt such as heminapadisylate methanolate or heminapadisylate ethanolate, or a freebase (Form I or II). Napadisylate salts are also sometimes referred to as naphthalene-1,5-disulfonic acid salts.

Definitions

When describing the compounds, compositions, methods and processes of the invention, the following terms have the following meanings unless otherwise indicated.

The term "solvate" means a crystal form, where molecules of solvent are incorporated in the unit cell of the crystal lattice, e.g., a heminapadisylate salt of the compound of formula I, and molecules of a solvent such as ethanol or methanol. The solvate may include one or more molecules of solvent, but the number of solvent molecules may also be a fraction of one such as one-half or one-fourth. In the present invention, an exemplary solvate crystal comprises one molecule of ethanol or methanol solvent, per 0.5 molecule of naphthalene-1,5-disulfonic acid counterion, and one molecule of the compound of formula I. Solvates typically have a substantially fixed molar ratio of solute and solvent. This term also includes clathrates, including clathrates with water. Representative solvents include, by way of example, water, methanol, ethanol, isopropanol, acetic acid and the like.

When the solvent molecule in a solvate crystal is water, the crystal is called a hydrate, which is one class of solvates.

The term "Form I" refers to the crystalline freebase that is prepared by a method that uses isopropanol and ethyl acetate as the solvent system. The term "Form II" refers to the crystalline freebase that is prepared by a method that uses isopropanol as the solvent system.

The term "melting point" as used herein means the temperature at which the maximum endothermic heat flow is observed by differential scanning calorimetry, for the thermal transition that corresponds to the solid-to-liquid phase change.

The term "therapeutically effective amount" means an amount sufficient to effect treatment when administered to a patient in need of treatment. For example, a therapeutically effective amount for antagonizing a muscarinic receptor is that amount which will achieve the desired antagonizing effect. Similarly, a therapeutically effective amount for treating a pulmonary disorder is that amount that will achieve the desired therapeutic result, which may be disease prevention, amelioration, suppression or alleviation, as described below.

The term "treating" or "treatment" as used herein means the treating or treatment of a disease or medical condition (such as COPD) in a patient such as a mammal (particularly a human) that includes:
  (a) preventing the disease or medical condition from occurring, i.e., prophylactic treatment of a patient believed to be at risk of contracting or being pre-disposed to such disease or medical condition;
  (b) ameliorating the disease or medical condition, i.e., eliminating or causing regression of the disease or medical condition in a patient having such disease or medical condition;
  (c) suppressing the disease or medical condition, i.e., slowing or arresting the development of the disease or medical condition in a patient having such disease or medical condition; or
  (d) alleviating the symptoms of the disease or medical condition in a patient having such disease or medical condition.

The term "pharmaceutically acceptable" refers to a material that is not biologically or otherwise undesirable. For example, the term "pharmaceutically acceptable carrier" refers to a material that can be incorporated into a composition and administered to a patient without causing undesirable biological effects or interacting in a deleterious manner with other components of the composition. Such pharmaceutically acceptable materials typically have met the required standards of toxicological and manufacturing testing, and include those materials identified as suitable inactive ingredients by the U.S. Food and Drug administration.

The term "unit dosage form" refers to a physically discrete unit suitable for dosing a patient, i.e., each unit containing a predetermined quantity of a compound of the invention calculated to produce the desired therapeutic effect either alone or in combination with one or more additional units. For example, such unit dosage forms may be capsules, tablets, pills, and the like.

Synthesis

The crystalline compounds of the invention can be synthesized from readily available starting materials as described below and in the Examples. There are several methods that can be used to produce the crystalline compounds of the invention. It is noted, however, that the crystalline content as well as the habit of the crystals (size and shape) may vary, based partly upon the method of preparation, as well as on the solvent composition. The crystals have been observed in various habits, including rhombohedral, needles, plates, clusters, and as variations of such.

It will be appreciated that while specific process conditions (i.e. crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 20 to 30° C. In other instances, reactions or crystallizations were conducted at room temperature and the temperature was actually measured and noted to be about 22° C.

Generally, the crystallizations are conducted in a suitable inert diluent or solvent system, examples of which include, but are not limited to, methanol, ethanol, isopropanol, isobutanol, ethyl acetate, acetonitrile, dichloromethane, methyl t-butyl ether, and the like, and mixtures thereof, optionally containing water. Upon completion of any of the foregoing crystallizations, the crystalline compounds can be isolated from the reaction mixture by any conventional means such as precipitation, concentration, centrifugation and the like.

The biphenyl-2-ylcarbamic acid 1-[2-({3-[2-(4-hydroxybenzylamino)ethylcarbamoyl]benzoyl}methylamino)ethyl] piperidin-4-yl ester employed in the invention can be readily prepared from commercially available starting materials and reagents using the procedures described in the Examples, or using the procedures described in the commonly-assigned U.S. applications described in the Background section of this application. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Hemiedisylate Salt Crystal

A hemiedisylate salt crystal of the invention typically contains about 1.0±0.1 molar equivalents of freebase (the compound of formula I) per about 0.5±0.1 molar equivalent of counterion (1,2 ethane disulfonic acid).

In general, a crystalline hemiedisylate salt can be prepared by contacting biphenyl-2-ylcarbamic acid 1-[2-({3-[2-(4-hydroxybenzylamino)ethylcarbamoyl]benzoyl}methylamino) ethyl]piperidin-4-yl ester with 1,2 ethane disulfonic acid. For example, the ester can be dissolved in an inert diluent such as a mixture of methanol and acetonitrile, then contacted with a free acid solution of 1,2 ethane disulfonic acid dissolved in the same solvent system (methanol and acetonitrile). Generally, this reaction is conducted at a temperature ranging from about 20 to 30° C. (e.g., about 22° C.), heated to a temperature ranging from about 40 to 60° C. (e.g. about 50° C.), then cooled to a temperature ranging from about 20 to 30° C. (e.g., about 22° C.).

Heminapadisylate Methanolate Crystal

A heminapadisylate methanolate crystal of the invention typically contains about 1.0±0.1 molar equivalent of freebase (the compound of formula I) per about 0.5±0.1 molar equivalents of counterion (naphthalene-1,5-disulfonic acid) and about 1.0±0.1 molar equivalents of solvent (methanol).

In general, a crystalline heminapadisylate methanolate of the compound of formula I can be prepared by contacting biphenyl-2-ylcarbamic acid 1-[2-({3-[2-(4-hydroxybenzylamino)ethylcarbamoyl]benzoyl}methylamino)ethyl]piperidin-4-yl ester with naphthalene-1,5-disulfonic acid and methanol. For example, the ester can be dissolved in methanol and an inert diluent such as acetonitrile, then contacted with a free acid solution of naphthalene-1,5-disulfonic acid dissolved in the same solvent system (methanol and acetonitrile). Generally, this reaction is conducted at a temperature ranging from about 20 to 30° C. (e.g., about room temperature), heated to a temperature ranging from about 25 to 35° C. (e.g. about 30° C.), heated to a second temperature ranging from about 40 to 60° C. (e.g. about 50° C.), then cooled to a temperature ranging from about 20 to 30° C. (e.g., about room temperature).

Naphthalene-1,5-disulfonic acid (also known as Armstrong's Acid) is commercially available from, for example, Aldrich, Milwaukee, Wis. In one embodiment, the 1naphthalene-1,5-disulfonic acid employed in preparing the crystalline compounds of the invention is a tetrahydrate. If desired, the naphthalene-1,5-disulfonic acid tetrahydrate employed in the invention can be recrystallized from, for example, acetonitrile prior to use.

Heminapadisylate Ethanolate Crystal

A heminapadisylate ethanolate crystal of the invention typically contains about 1.0±0.1 molar equivalent of freebase (the compound of formula I) per about 0.5±0.1 molar equivalents of counterion (naphthalene-1,5-disulfonic acid) and about 1.0±0.1 molar equivalents of solvent (ethanol).

In general, a crystalline heminapadisylate ethanolate of the compound of formula I can be prepared by contacting biphenyl-2-ylcarbamic acid 1-[2-({3-[2-(4-hydroxybenzylamino)ethylcarbamoyl]benzoyl}methylamino)ethyl]piperidin-4-yl ester with naphthalene-1,5-disulfonic acid and ethanol. For example, the ester and solid naphthalene-1,5-disulfonic acid can be dissolved in ethanol, while being heated to a temperature ranging from about 35 to 45° C. (e.g. about 40° C.). Crystallization can then be induced by adding an inert diluent such as acetonitrile and cooling to a temperature ranging from about 20 to 30° C. (e.g., about 22° C.).

Heminapadisylate Salt Crystal (Desolvate)

A heminapadisylate salt crystal (desolvate) of the invention typically contains about 1.0±0.1 molar equivalent of freebase (the compound of formula I) per about 0.5±0.1 molar equivalents of counterion (naphthalene-1,5-disulfonic acid).

In general, a crystalline heminapadisylate salt of the compound of formula I can be prepared by contacting biphenyl-2-ylcarbamic acid 1-[2-({3-[2-(4-hydroxybenzylamino)ethylcarbamoyl]benzoyl}methylamino)ethyl]piperidin-4-yl ester with naphthalene-1,5-disulfonic acid. A heminapadisylate salt can also be prepared from a solvate form of such salt. For example, heminapadisylate methanolate or ethanolate can be dried at a moderate temperature ranging from about 40 to 60° C. (e.g. about 50° C. overnight then about 40° C. for several days) to produce the heminapadisylate salt (desolvated). This crystallization can be conducted under vacuum to speed up the desolvation process. Alternately, the desolvated heminapadisylate crystal form can be prepared by heating the crystalline heminapadisylate methanolate or ethanolate form at a high temperature ranging from about 90 to 110° C. (e.g. about 100° C. for several hours). The desolvated heminapadisylate crystal form can also be prepared by reslurrying the crystalline heminapadisylate methanolate or ethanolate form in an excess of an inert diluent, usually one that is different from the solvent that makes up the solvate (e.g., acetonitrile instead of methanol or ethanol); this reaction is typically conducted at a temperature ranging from about 5 to 50° C. (e.g., about 5° C., about 20° C., or about 50° C.).

Dimethylformamide and dimethylsulfoxide are also suitable solvents for use in preparing heminapadisylate solvate or desolvate crystals, and are particularly useful when used in small amounts, for example, 1-5% of the total solvent mixture. The inclusion of such solvents has been found to greatly reduce the encrustation tendency during the crystallization process.

Freebase Crystal (Forms I and II)

In general, a crystalline freebase of the compound of formula I can be prepared by contacting biphenyl-2-ylcarbamic acid 1-[2-({3-[2-(4-hydroxybenzylamino)ethylcarbamoyl]benzoyl}methylamino)ethyl]piperidin-4-yl ester with an inert diluent.

To prepare one form of a crystalline freebase (Form I), the ester is typically contacted with an inert diluent (e.g., ethyl acetate and isopropanol). Generally, this reaction is conducted at a temperature ranging from about 20 to 30° C. (e.g., about room temperature). The solution can then be washed with water and the organic phase dried then filtered.

To prepare another form of a crystalline freebase (Form II), the ester is typically contacted with an inert diluent (e.g., isopropanol). Generally, this reaction is conducted at a temperature ranging from about 20 to 30° C. (e.g., about 22° C.). After a suitable amount of time, crystals will be observed, at which point the mother liquor can be decanted and the crystals washed with an aqueous mixture (e.g., isopropanol and water).

A crystalline freebase (Form II) can also be prepared by forming a seed crystal of a crystalline freebase (synthesized as described above), forming a crystalline freebase by contacting the ester with an inert diluent and dissolving the resulting crystalline ester to form a solution, and adding the seed crystal to the solution. In one embodiment, the ester is typically contacted with an inert diluent (e.g., isopropanol and water). Generally, this reaction is conducted at a temperature ranging from about 20 to 30° C. (e.g., about 22° C.). The seed crystal of a crystalline freebase of the ester is then added, and the reaction vessel left at the same temperature (e.g., about 22° C.). After crystals have formed (e.g., overnight), further crystallization can be achieved by cooling to a temperature ranging from about 0 to 10° C. (e.g., about 4° C.).

Crystalline Properties

Among other advantages, it has been discovered that forming a crystalline salt, solvate of such a salt or a freebase of the compound of formula I, is useful for purifying the compound itself. For example, a crystalline heminapadisylate salt of the invention has a purity of 99%.

As is well known in the field of powder x-ray diffraction, relative peak heights of PXRD spectra are dependent on a number of factors relating to sample preparation and instrument geometry, while peak positions are relatively insensitive to experimental details. PXRD patterns were obtained as set forth in Example 8. Thus, in one embodiment, the crystalline compounds of the invention are characterized by a PXRD pattern having certain peak positions.

A crystalline hemiedisylate salt of the compound of formula I is characterized by a PXRD pattern in which the peak positions are substantially in accordance with those shown in FIG. 1. Those peaks are listed below, in order of descending relative intensity.

| I %  | 2-Theta |
|------|---------|
| 100  | 21.210  |
| 93.1 | 19.262  |
| 87.9 | 25.080  |
| 66   | 13.922  |
| 50.1 | 17.460  |
| 38   | 23.639  |
| 25.3 | 29.549  |
| 24.7 | 16.318  |
| 22.7 | 23.161  |
| 19.3 | 8.136   |
| 18.3 | 22.415  |
| 17.4 | 27.003  |
| 16.5 | 30.840  |
| 14.6 | 12.567  |
| 14   | 9.899   |
| 13.4 | 11.281  |
| 9.8  | 33.099  |
| 8.2  | 38.889  |
| 7.9  | 34.162  |
| 7.3  | 28.448  |
| 7.3  | 36.057  |
| 7    | 9.118   |
| 6.8  | 32.021  |

Thus, in one embodiment, the crystalline hemiedisylate salt of the present invention is characterized by a powder x-ray diffraction (PXRD) pattern having two or more diffraction peaks at 2θ values selected from 8.14±0.20, 9.12±0.20, 9.90±0.20, 11.28±0.20, 12.57±0.20, 13.92±0.20, 16.32±0.20, 17.46±0.20, 19.26±0.20, 21.21±0.20, 22.42±0.20, 23.16±0.20, 23.64±0.20, 25.08±0.20, 27.00±0.20, 28.45±0.20, 29.55±0.20, 30.84±0.20, 32.02±0.20, 33.10±0.20, 34.16±0.20, 36.06±0.20, and 38.89±0.20. In particular, in this embodiment, this crystalline form is characterized by a powder x-ray diffraction pattern comprising diffraction peaks at 2θ values of 8.14±0.20, 9.90±0.20, 12.57±0.20, 13.92±0.20, 16.32±0.20, 17.46±0.20, 19.26±0.20, 21.21±0.20, 22.42±0.20, 23.16±0.20, 23.64±0.20, 25.08±0.20, 27.00±0.20, 29.55±0.20, and 30.84±0.20.

Figure 5:
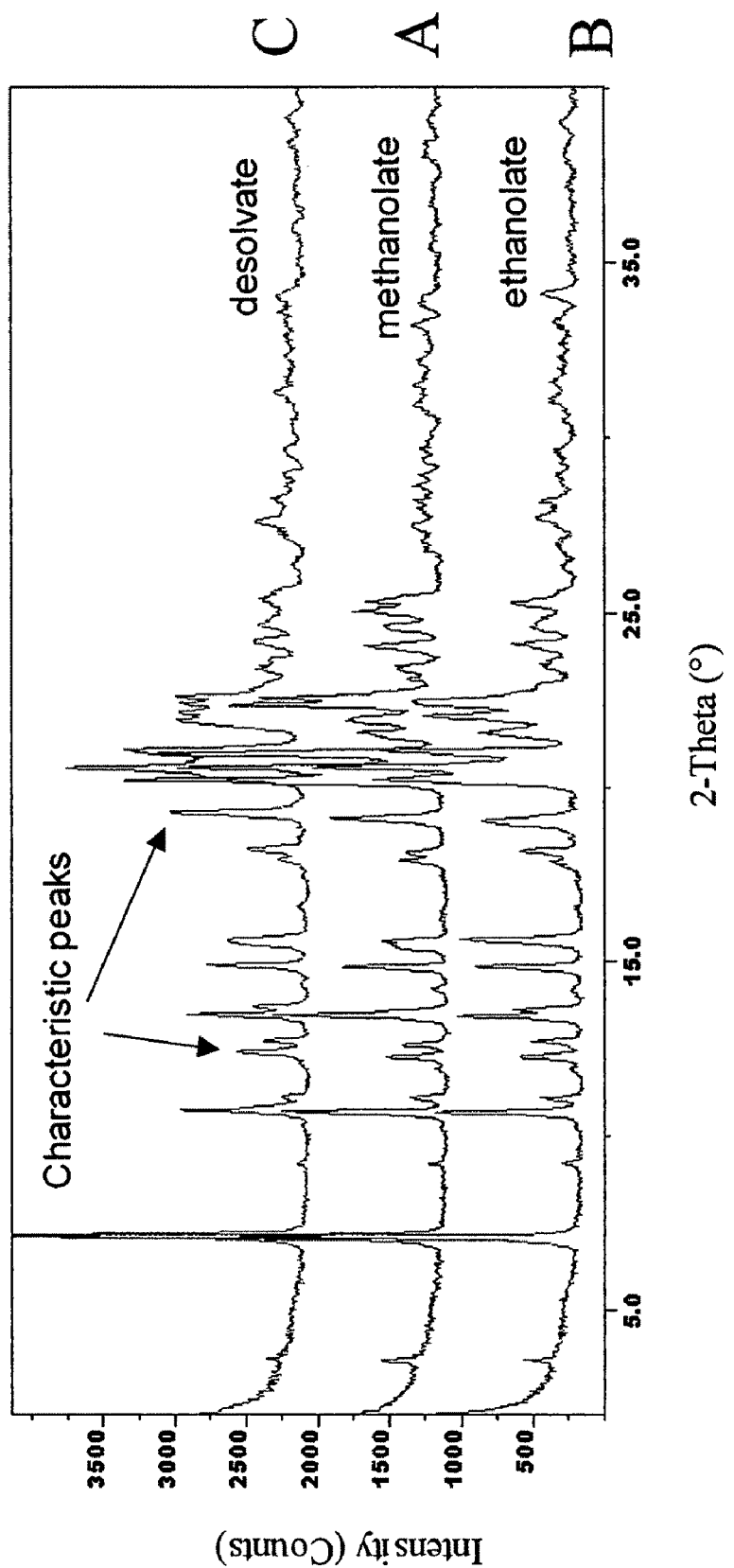
FIGS. 5A-5C show PXRD patterns of a crystalline heminapadisylate methanolate of the compound of formula I (FIG. 5A, center line), a crystalline heminapadisylate ethanolate of the compound of formula I (FIG. 5B, bottom line), and a crystalline heminapadisylate salt (desolvate.

A crystalline heminapadisylate methanolate of the compound of formula I is characterized by a PXRD pattern in which the peak positions are substantially in accordance with those shown in FIG. 5A. Those peaks are listed below, in order of descending relative intensity.

| I %  | 2-Theta |
|------|---------|
| 100  | 7.132   |
| 97.7 | 20.572  |
| 93.6 | 20.243  |
| 59.8 | 21.045  |
| 57   | 22.552  |
| 55.7 | 10.731  |
| 53.8 | 13.490  |
| 49.8 | 19.129  |
| 47.4 | 15.564  |
| 42.6 | 22.037  |
| 31.8 | 14.816  |
| 27.4 | 25.279  |
| 25.6 | 21.636  |
| 24.9 | 12.238  |
| 22.3 | 24.053  |
| 20   | 18.167  |

-continued

| I %  | 2-Theta |
|------|---------|
| 18.7 | 24.681  |
| 14.8 | 12.732  |
| 14.6 | 27.587  |
| 14.3 | 34.126  |
| 13.1 | 23.464  |
| 13.1 | 28.249  |
| 12.5 | 11.113  |
| 12.3 | 17.880  |
| 12   | 3.542   |
| 11.8 | 33.316  |
| 7.5  | 16.484  |
| 7.4  | 31.614  |
| 7.2  | 9.337   |
| 7.2  | 27.045  |
| 7    | 31.039  |
| 6.9  | 6.534   |
| 6.4  | 29.393  |
| 6.1  | 29.939  |
| 5.9  | 38.991  |
| 5.7  | 26.415  |
| 5.7  | 37.331  |
| 5.2  | 38.175  |

Thus, in one embodiment, the crystalline heminapadisylate methanolate of the present invention is characterized by a powder x-ray diffraction (PXRD) pattern having two or more diffraction peaks at 2θ values selected from 3.54±0.20, 6.53±0.20, 7.13±0.20, 9.34±0.20, 10.73±0.20, 11.11±0.20, 12.24±0.20, 12.73±0.20, 13.49±0.20, 14.82±0.20, 15.56±0.20, 16.48±0.20, 17.88±0.20, 18.17±0.20, 19.13±0.20, 20.24±0.20, 20.57±0.20, 21.05±0.20, 21.64±0.20, 22.04±0.20, 22.55±0.20, 23.46±0.20, 24.05±0.20, 24.68±0.20, 25.28±0.20, 26.42±0.20, 27.05±0.20, 27.59±0.20, 28.25±0.20, 29.39±0.20, 29.94±0.20, 31.04±0.20, 31.61±0.20, 33.32±0.20, 34.13±0.20, 37.33±0.20, 38.18±0.20, and 38.99±0.20. In particular, in this embodiment, this crystalline form is characterized by a powder x-ray diffraction pattern comprising diffraction peaks at 2θ values of 7.13±0.20, 10.73±0.20, 12.24±0.20, 12.73±0.20, 13.49±0.20, 14.82±0.20, 15.56±0.20, 18.17±0.20, 19.13±0.20, 20.24±0.20, 20.57±0.20, 21.05±0.20, 21.64±0.20, 22.04±0.20, 22.55±0.20, 24.05±0.20, 24.68±0.20, 25.28±0.20, 27.59±0.20, and 34.13±0.20.

A crystalline heminapadisylate ethanolate of the compound of formula I is characterized by a PXRD pattern in which the peak positions are substantially in accordance with those shown in FIG. 5B. Those peaks are listed below, in order of descending relative intensity.

| I %  | 2-Theta |
|------|---------|
| 100  | 7.042   |
| 92.6 | 22.405  |
| 87.7 | 20.570  |
| 73   | 20.178  |
| 70.4 | 10.614  |
| 69.3 | 14.864  |
| 39.5 | 25.164  |
| 37.9 | 18.203  |
| 34.6 | 21.387  |
| 32.8 | 22.124  |
| 30   | 13.547  |
| 26.7 | 26.540  |
| 26.3 | 15.627  |
| 26   | 18.860  |
| 22.6 | 31.755  |
| 20.7 | 17.750  |

-continued

| I % | 2-Theta |
|---|---|
| 19.7 | 21.021 |
| 17 | 12.603 |
| 16.9 | 32.606 |
| 15.1 | 24.770 |
| 14.6 | 27.861 |
| 14.2 | 29.066 |
| 14.1 | 12.233 |
| 12.8 | 34.167 |
| 12.6 | 11.922 |
| 12.2 | 9.309 |
| 12.1 | 33.353 |
| 9.8 | 11.116 |
| 9.1 | 29.688 |
| 8.9 | 28.215 |
| 8.7 | 3.477 |
| 8.6 | 23.571 |
| 8.6 | 24.196 |
| 7.1 | 38.176 |
| 5.7 | 31.104 |
| 5.3 | 27.101 |
| 5.3 | 30.559 |
| 5.2 | 37.314 |
| 4.8 | 35.929 |
| 3.7 | 38.787 |
| 3.1 | 36.235 |

Thus, in one embodiment, the crystalline heminapadisylate ethanolate of the present invention is characterized by a powder x-ray diffraction (PXRD) pattern having two or more diffraction peaks at 2θ values selected from 3.48±0.20, 7.04±0.20, 9.31±0.20, 10.61±0.20, 11.12±0.20, 11.92±0.20, 12.23±0.20, 12.60±0.20, 13.55±0.20, 14.86±0.20, 15.63±0.20, 17.75±0.20, 18.20±0.20, 18.86±0.20, 20.18±0.20, 20.57±0.20, 21.02±0.20, 21.39±0.20, 22.12±0.20, 22.41±0.20, 23.57±0.20, 24.20±0.20, 24.77±0.20, 25.16±0.20, 26.54±0.20, 27.10±0.20, 27.86±0.20, 28.22±0.20, 29.07±0.20, 29.69±0.20, 30.56±0.20, 31.10±0.20, 31.76±0.20, 32.61±0.20, 33.35±0.20, 34.17±0.20, 35.93±0.20, 36.24±0.20, 37.31±0.20, 38.18±0.20, and 38.79±0.20. In particular, in this embodiment, this crystalline form is characterized by a powder x-ray diffraction pattern comprising diffraction peaks at 2θ values of 7.04±0.20, 10.61±0.20, 12.23±0.20, 12.60±0.20, 13.55±0.20, 14.86±0.20, 15.63±0.20, 17.75±0.20, 18.20±0.20, 18.86±0.20, 20.18±0.20, 20.57±0.20, 21.02±0.20, 21.39±0.20, 22.12±0.20, 22.41±0.20, 24.77±0.20, 25.16±0.20, 26.54±0.20, 27.86±0.20, 29.07±0.20, 31.76±0.20, and 32.61±0.20.

Figure 10:
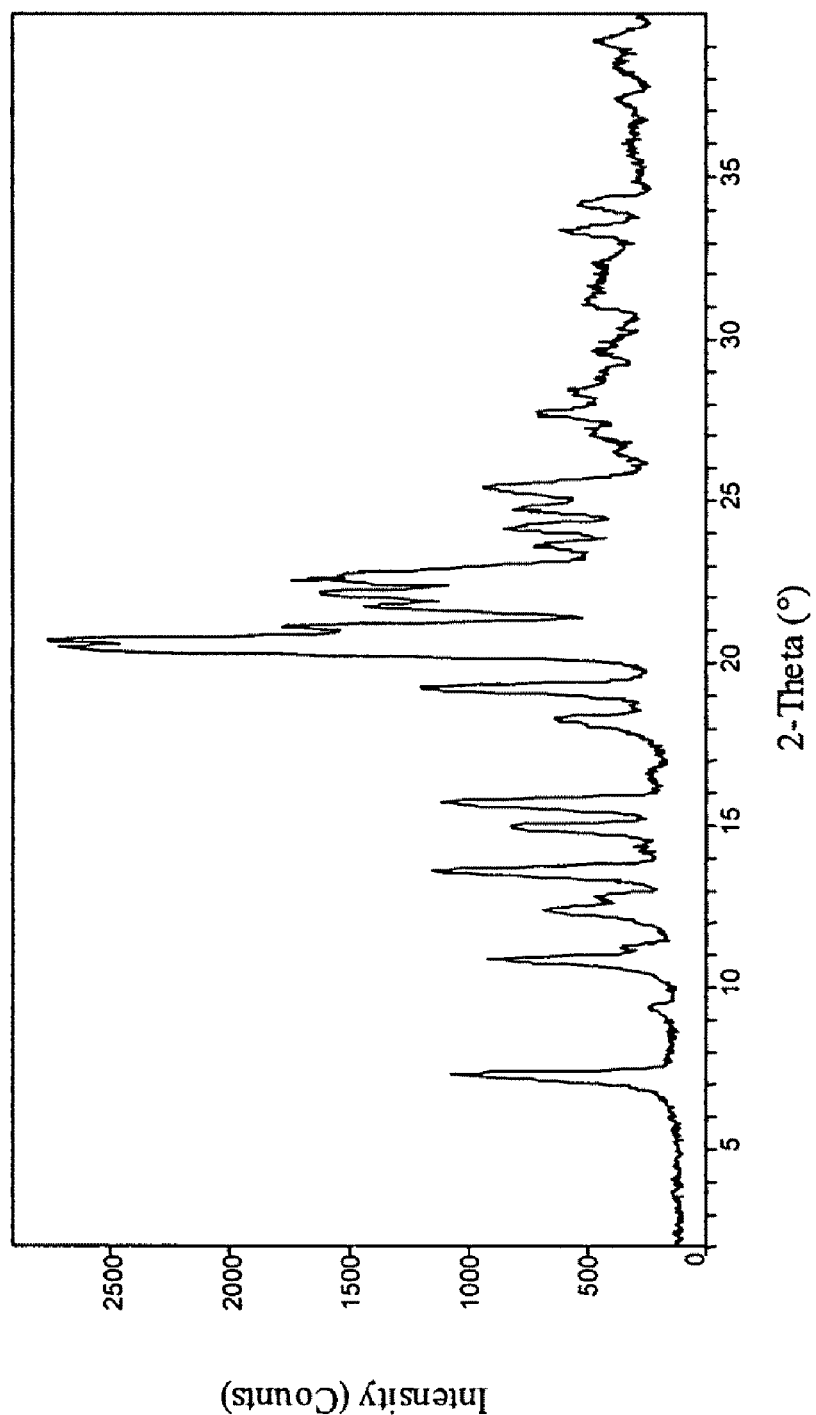
FIG. 10 shows a PXRD pattern of a crystalline heminapadisylate salt (desolvate) of the compound of formula I (also depicted as FIG. 5C). This crystalline salt is further characterized by the DSC trace and TGA trace in FIG. 11 (a DSC trace of the desolvate in acetonitrile is also depicted in FIG. 6C), the DMS trace in FIG. 12, and the polarized light micrographic image in FIG. 13.

A crystalline heminapadisylate salt of the compound of formula I is characterized by a PXRD pattern in which the peak positions are substantially in accordance with those shown in FIG. 10 (and FIG. 5C). Those peaks are listed below, in order of descending relative intensity.

| I % | 2-Theta |
|---|---|
| 100 | 20.480 |
| 47.5 | 21.111 |
| 44.2 | 22.553 |
| 42.6 | 22.186 |
| 37.8 | 19.249 |
| 37.7 | 7.309 |
| 37.5 | 13.610 |
| 35.3 | 15.738 |
| 33.6 | 21.742 |
| 30.5 | 10.879 |
| 23.5 | 25.430 |
| 23.4 | 14.989 |

-continued

| I % | 2-Theta |
|---|---|
| 19.2 | 12.381 |
| 15.3 | 24.167 |
| 14.7 | 18.290 |
| 14.6 | 24.742 |
| 12.7 | 27.765 |
| 11.9 | 33.378 |
| 10.3 | 34.163 |
| 10.2 | 12.800 |
| 8 | 23.580 |
| 8 | 28.429 |
| 7 | 39.197 |
| 6.7 | 11.265 |
| 6.3 | 29.661 |
| 5.7 | 31.102 |
| 5.1 | 29.923 |
| 4.8 | 37.428 |
| 4 | 9.38 |
| 3.5 | 27.054 |
| 3.5 | 38.360 |
| 3 | 36.015 |
| 2.4 | 16.603 |

Thus, in one embodiment, the crystalline heminapadisylate salt of the present invention is characterized by a powder x-ray diffraction (PXRD) pattern having two or more diffraction peaks at 2θ values selected from 7.31±0.20, 9.38±0.20, 10.88±0.20, 11.27±0.20, 12.38±0.20, 12.80±0.20, 13.61±0.20, 14.99±0.20, 15.74±0.20, 16.60±0.20, 18.29±0.20, 19.25±0.20, 20.48±0.20, 21.11±0.20, 21.74±0.20, 22.19±0.20, 22.55±0.20, 23.58±0.20, 24.17±0.20, 24.74±0.20, 25.43±0.20, 27.05±0.20, 27.77±0.20, 28.43±0.20, 29.66±0.20, 29.92±0.20, 31.10±0.20, 33.38±0.20, 34.16±0.20, 36.02±0.20, 37.43±0.20, 38.36±0.20, and 39.20±0.20. In particular, in this embodiment, this crystalline form is characterized by a powder x-ray diffraction pattern comprising diffraction peaks at 2θ values of 7.31±0.20, 10.88±0.20, 12.38±0.20, 13.61±0.20, 14.99±0.20, 15.74±0.20, 18.29±0.20, 19.25±0.20, 20.48±0.20, 21.11±0.20, 21.74±0.20, 22.19±0.20, 22.55±0.20, 24.17±0.20, and 25.43±0.20.

Figure 14:
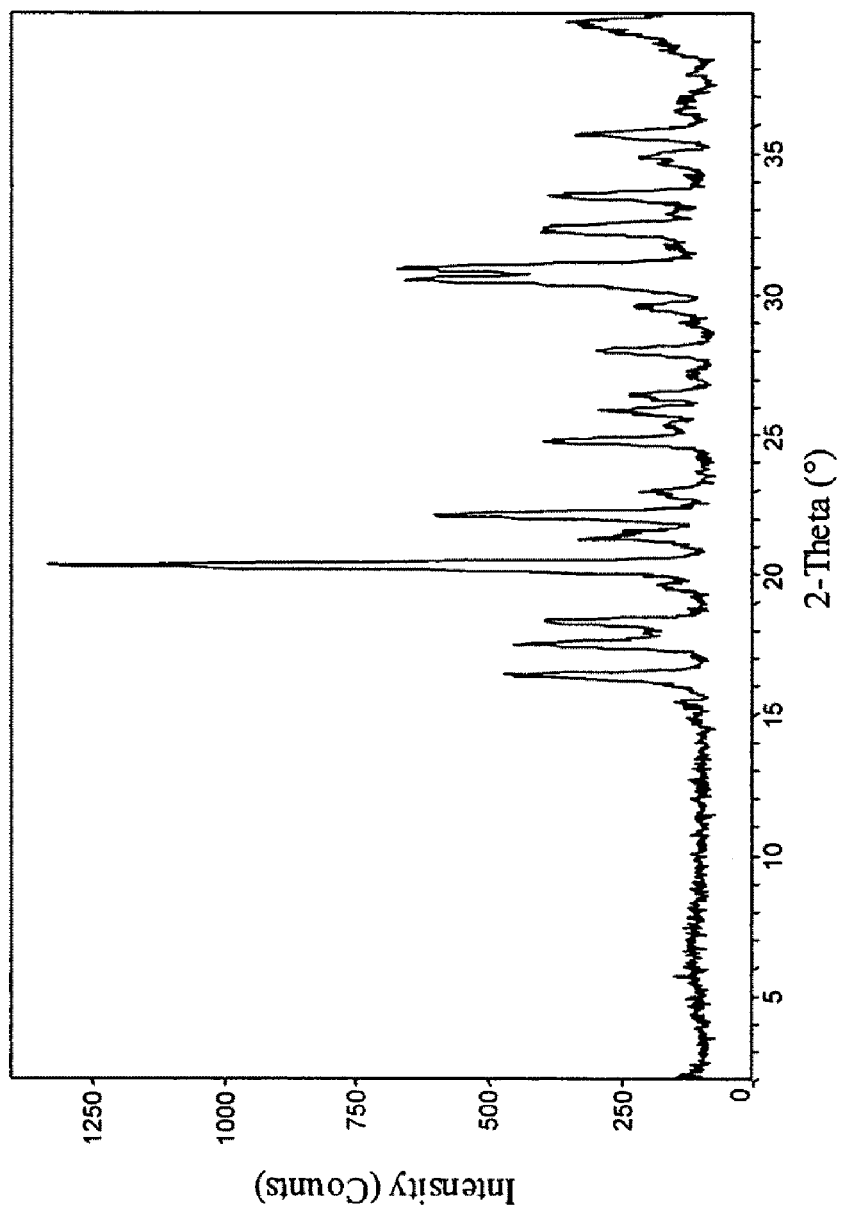
FIG. 14 shows a PXRD pattern of one form (Form I) of a crystalline freebase of the compound of formula I. This crystalline freebase is further characterized by the DSC trace and the TGA trace in FIG. 15.

One crystalline freebase (Form I) of the compound of formula I is characterized by a PXRD pattern in which the peak positions are substantially in accordance with those shown in FIG. 14. Those peaks are listed below, in order of descending relative intensity.

| I % | 2-Theta |
|---|---|
| 100 | 20.329 |
| 44.6 | 30.892 |
| 43.9 | 30.501 |
| 38.7 | 22.130 |
| 30.1 | 16.426 |
| 26.2 | 17.483 |
| 23.2 | 24.745 |
| 21.8 | 32.389 |
| 21.8 | 33.499 |
| 19.4 | 35.660 |
| 18.4 | 18.345 |
| 17.3 | 28.039 |
| 17.1 | 21.294 |
| 14 | 25.878 |
| 9.7 | 26.451 |
| 9.5 | 22.978 |
| 9.5 | 29.599 |
| 9.3 | 34.906 |
| 6.3 | 34.644 |
| 5.5 | 19.629 |
| 4.5 | 15.417 |

-continued

| I % | 2-Theta |
|---|---|
| 4.2 | 25.371 |
| 4.2 | 36.893 |
| 4 | 36.471 |
| 3 | 27.164 |
| 3 | 37.839 |

Thus, in one embodiment, the crystalline freebase of the present invention is characterized by a powder x-ray diffraction (PXRD) pattern having two or more diffraction peaks at 2θ values selected from 15.42±0.20, 16.43±0.20, 17.48±0.20, 18.35±0.20, 19.63±0.20, 20.33±0.20, 21.29±0.20, 22.13±0.20, 22.98±0.20, 24.75±0.20, 25.37±0.20, 25.88±0.20, 26.45±0.20, 27.16±0.20, 28.04±0.20, 29.60±0.20, 30.50±0.20, 30.89±0.20, 32.39±0.20, 133.50±0.20, 34.64±0.20, 34.91±0.20, 35.66±0.20, 36.47±0.20, 36.89±0.20, and 37.84±0.20. In particular, in this embodiment, this crystalline form is characterized by a powder x-ray diffraction pattern comprising diffraction peaks at 2θ values of 16.43±0.20, 17.48±0.20, 18.35±0.20, 20.33±0.20, 21.29±0.20, 22.13±0.20, 24.75±0.20, 25.88±0.20, 26.45±0.20, 28.04±0.20, 30.50±0.20, 30.89±0.20, 32.39±0.20, 33.50±0.20, and 35.66±0.20.

Figure 16:
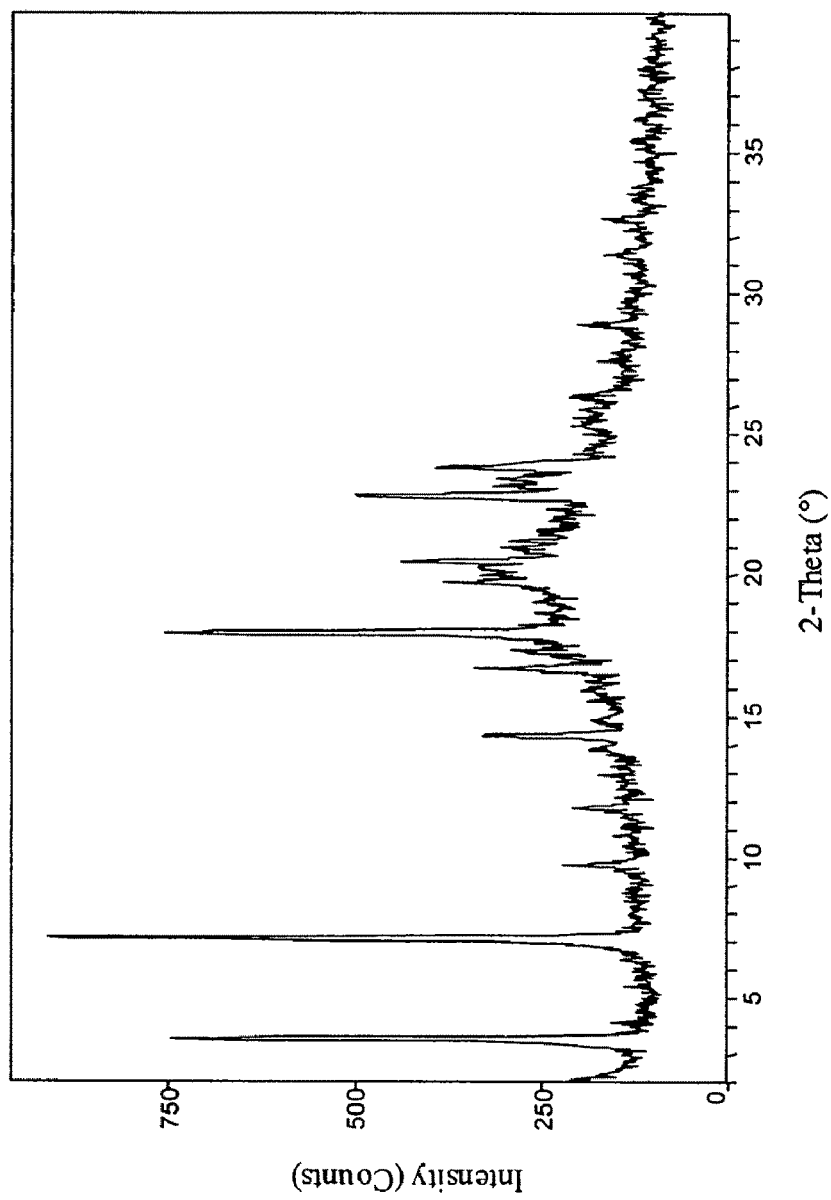
FIG. 16 shows a PXRD pattern of another form (Form II) of a crystalline freebase of the compound of formula I. This crystalline freebase is further characterized by the DSC trace in FIG. 17 and the TGA trace shown in FIG. 18.

Another crystalline freebase (From II) of the compound of formula I is characterized by a PXRD pattern in which the peak positions are substantially in accordance with those shown in FIG. 16. Those peaks are listed below, in order of descending relative intensity.

| I % | 2-Theta |
|---|---|
| 100 | 7.128 |
| 81.6 | 17.935 |
| 69.9 | 3.533 |
| 48.2 | 20.460 |
| 45.9 | 23.151 |
| 42.9 | 23.418 |
| 41.5 | 20.268 |
| 39.3 | 19.729 |
| 37.7 | 22.811 |
| 32.1 | 14.335 |
| 23.6 | 25.900 |
| 14.7 | 16.679 |
| 11.7 | 23.818 |
| 10.5 | 9.746 |
| 9.8 | 21.206 |
| 7.7 | 25.310 |
| 7.4 | 11.791 |
| 7.3 | 28.907 |
| 7.1 | 20.994 |
| 5.5 | 35.452 |
| 5.3 | 13.832 |
| 4.8 | 32.657 |
| 3.8 | 27.577 |
| 3.8 | 31.398 |
| 3.5 | 17.318 |
| 3.2 | 26.360 |

Thus, in one embodiment, a crystalline freebase of the present invention is characterized by a powder x-ray diffraction (PXRD) pattern having two or more diffraction peaks at 2θ values selected from 3.53±0.20, 7.13±0.20, 9.75±0.20, 11.79±0.20, 13.83±0.20, 14.34±0.20, 16.68±0.20, 17.32±0.20, 17.94±0.20, 19.73±0.20, 20.27±0.20, 20.46±0.20, 20.99±0.20, 21.21±0.20, 22.81±0.20, 23.15±0.20, 23.42±0.20, 23.82±0.20, 25.31±0.20, 25.90±0.20, 26.36±0.20, 27.58±0.20, 28.91±0.20, 31.40±0.20, 32.66±0.20, and 35.45±0.20. In particular, in this embodiment, this crystalline form is characterized by a powder x-ray diffraction pattern comprising diffraction peaks at 2θ values of 3.53±0.20, 7.13±0.20, 9.75±0.20, 14.34±0.20, 16.68±0.20, 17.94±0.20, 19.73±0.20, 20.27±0.20, 20.46±0.20, 21.21±0.20, 22.81±0.20, 23.15±0.20, 23.42±0.20, 23.82±0.20, and 25.90±0.20.

Figure 2:
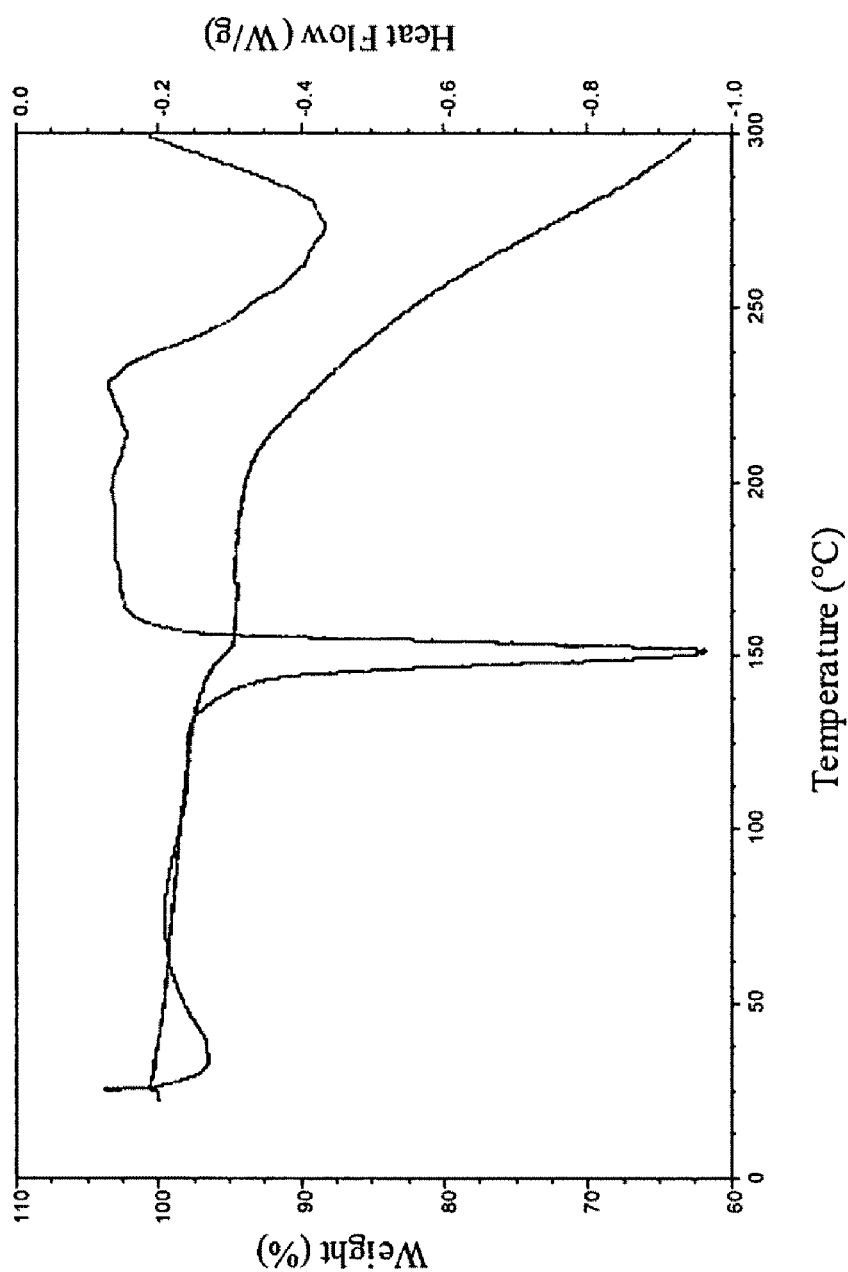
FIG. 2 shows a differential scanning calorimetry (DSC) trace and thermogravimetric analysis (TGA) trace for this crystalline salt.

Differential scanning calorimetry (DSC) traces were obtained as set forth in Example 9. Thus, in one embodiment, the crystalline compounds of the invention are 1characterized by their DSC trace. In one embodiment, a crystalline hemiedisylate salt of the compound of formula I is characterized by a DSC trace which shows a maximum endothermic heat flow at about 150° C., with one transition at about 151° C. and no thermal decomposition below about 190° C., as seen in FIG. 2. This crystal had a melting point of about 151° C.

Figure 6:
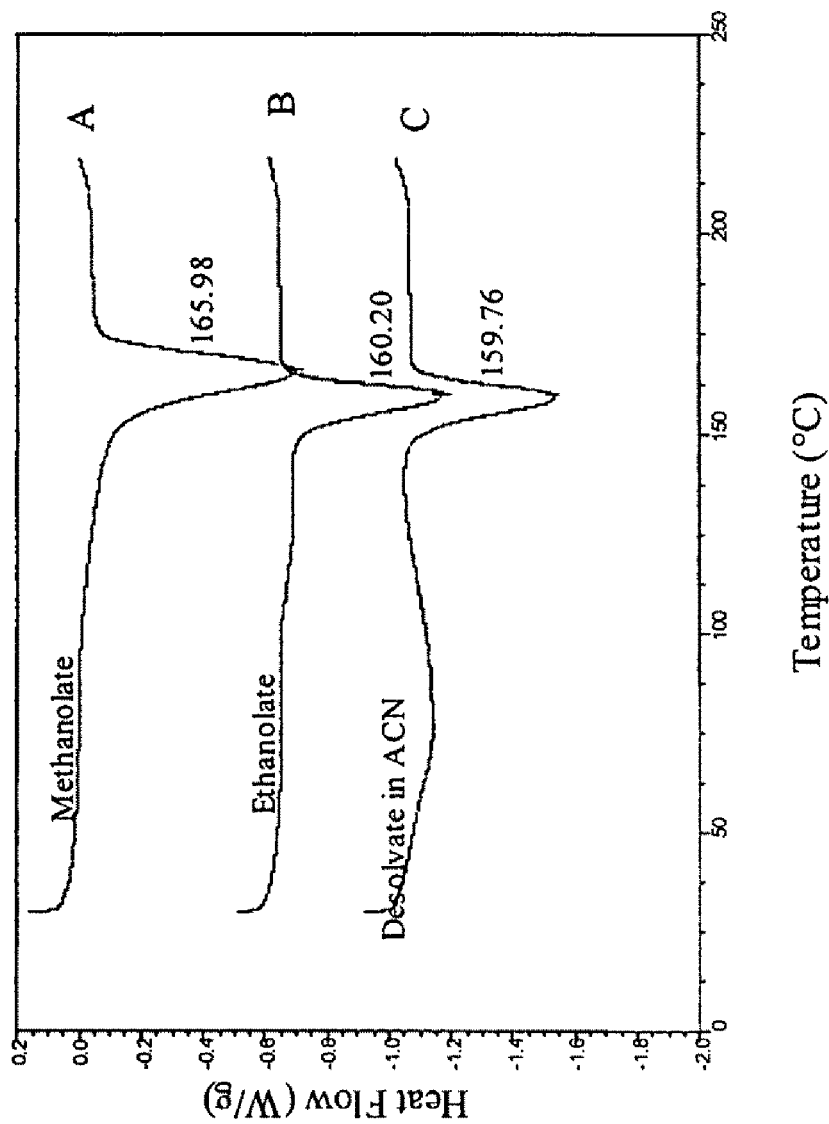
FIG. 6B shows DSC traces of a crystalline heminapadisylate ethanolate of the compound of formula I. The crystalline ethanolate is further characterized by the TGA trace shown in FIG. 8.

In one embodiment, a crystalline heminapadisylate methanolate of the compound of formula I is characterized by a DSC trace which shows a maximum endothermic heat flow at about 165° C., with one transition at about 165° C. and no thermal decomposition below about 195° C., as seen in FIG. 6A. This crystal had a melting point of about 165° C. In one embodiment, a crystalline heminapadisylate ethanolate of the compound of formula I is characterized by a DSC trace which shows a maximum endothermic heat flow at about 160° C., with one transition at about 160° C. and no thermal decomposition below about 195° C., as seen in FIG. 6B. This crystal had a melting point of about 160° C.

Figure 11:
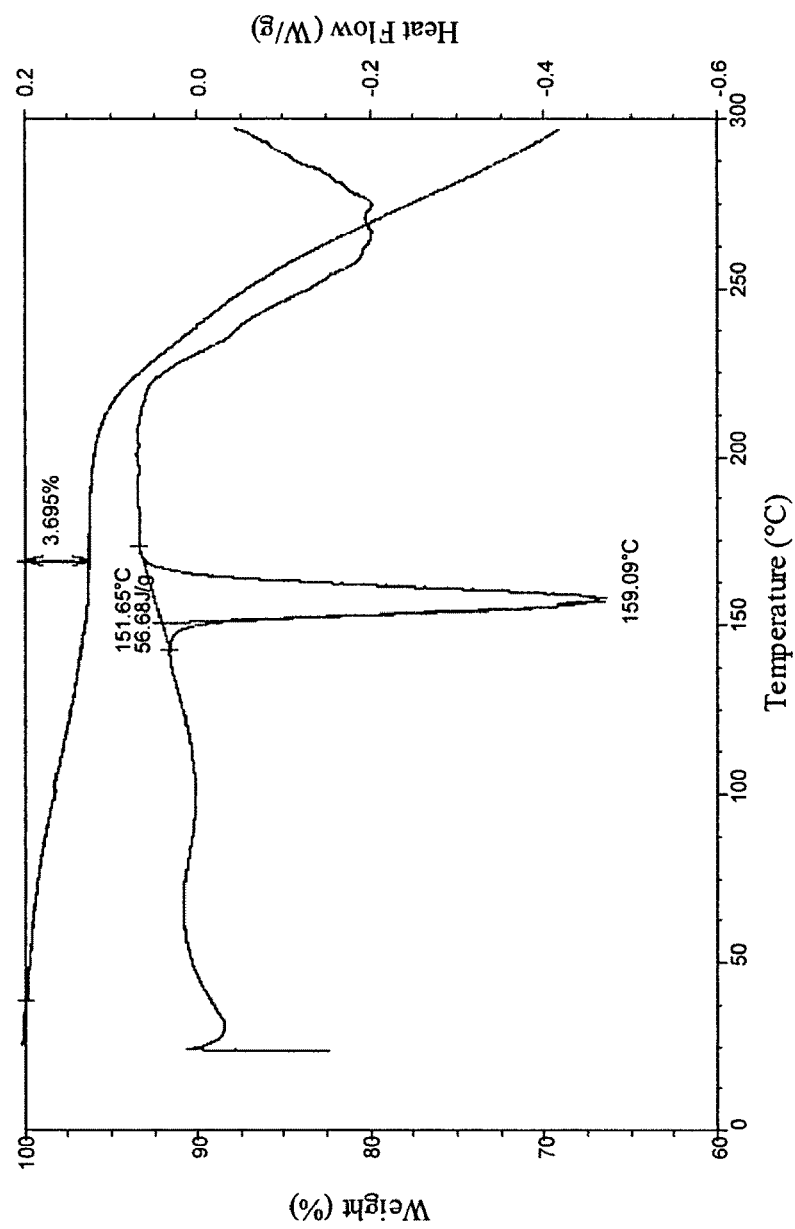

In one embodiment, a crystalline heminapadisylate salt of the compound of formula I is characterized by a DSC trace which shows a maximum endothermic heat flow at about 159° C., with one transition at about 159° C. and no thermal decomposition below about 220° C., as seen in FIG. 11. This crystal had a melting point of about 160° C.

Figure 15:
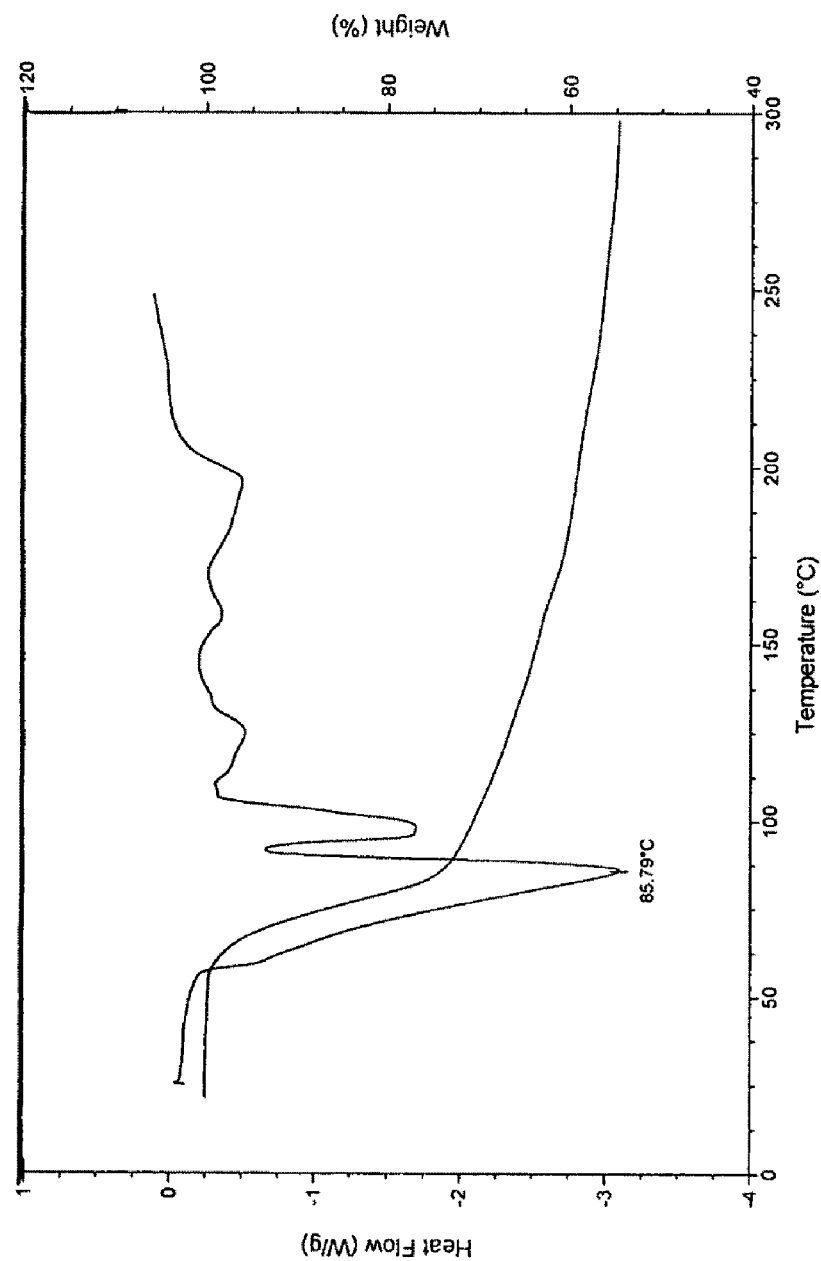
Figure 17:
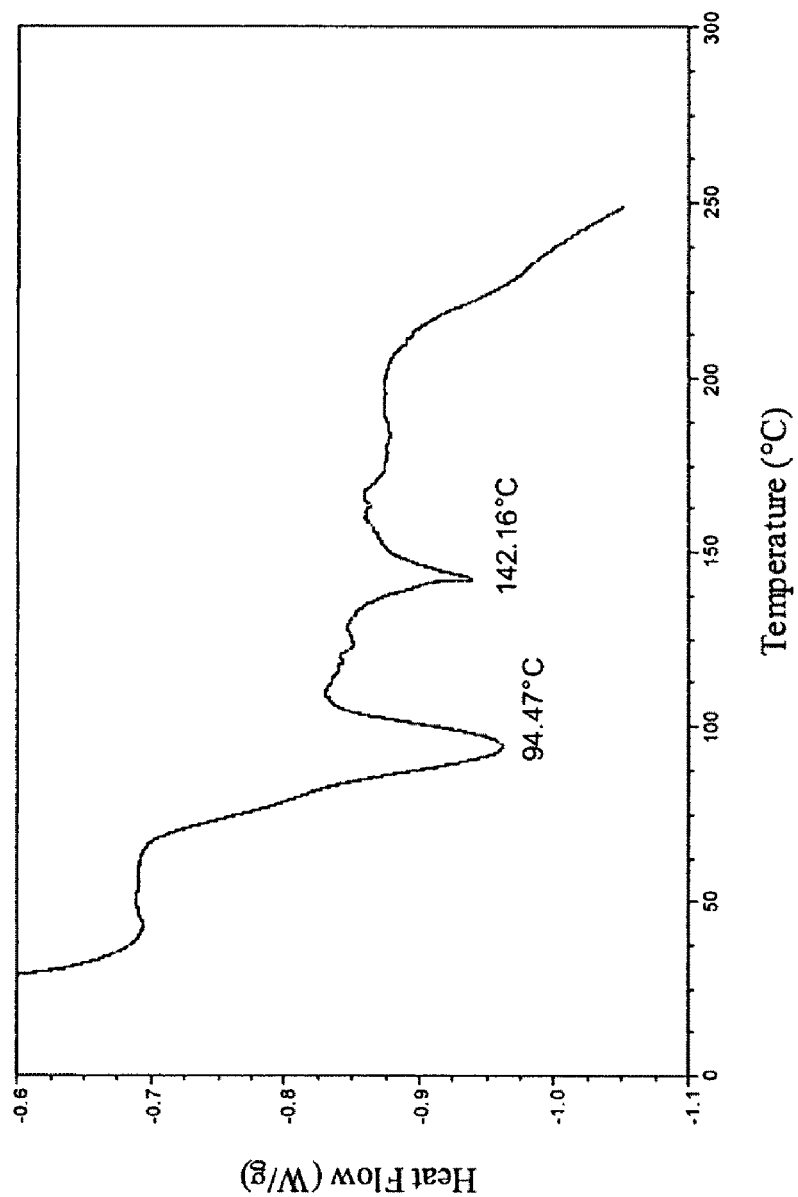

In one embodiment, a crystalline freebase (Form I) of the compound of formula I is characterized by a DSC trace which shows a maximum endothermic heat flow at about 85° C., with one transition at about 85.8° C. and no significant thermal decomposition below about 95° C., as seen in FIG. 15. This crystal had a melting point of about 99° C. In one embodiment, a crystalline freebase (Form II) of the compound of formula I is characterized by a DSC trace which shows a maximum endothermic heat flow at about 94° C., with one transition at about 94° C. and no thermal decomposition below about 110° C., as seen in FIG. 17. This crystal had a melting point of about 94° C.

Thermogravimetric analysis (TGA) was performed on the crystalline forms of the invention as described in Example 9. Thus, in one embodiment, the crystalline compounds of the invention are characterized by their TGA trace. In one embodiment, a crystalline hemiedisylate salt of the compound of formula I is characterized by a TGA trace which shows a loss of solvents and/or water (2%) at temperatures below about 150° C., as seen in FIG. 2.

Figure 7:
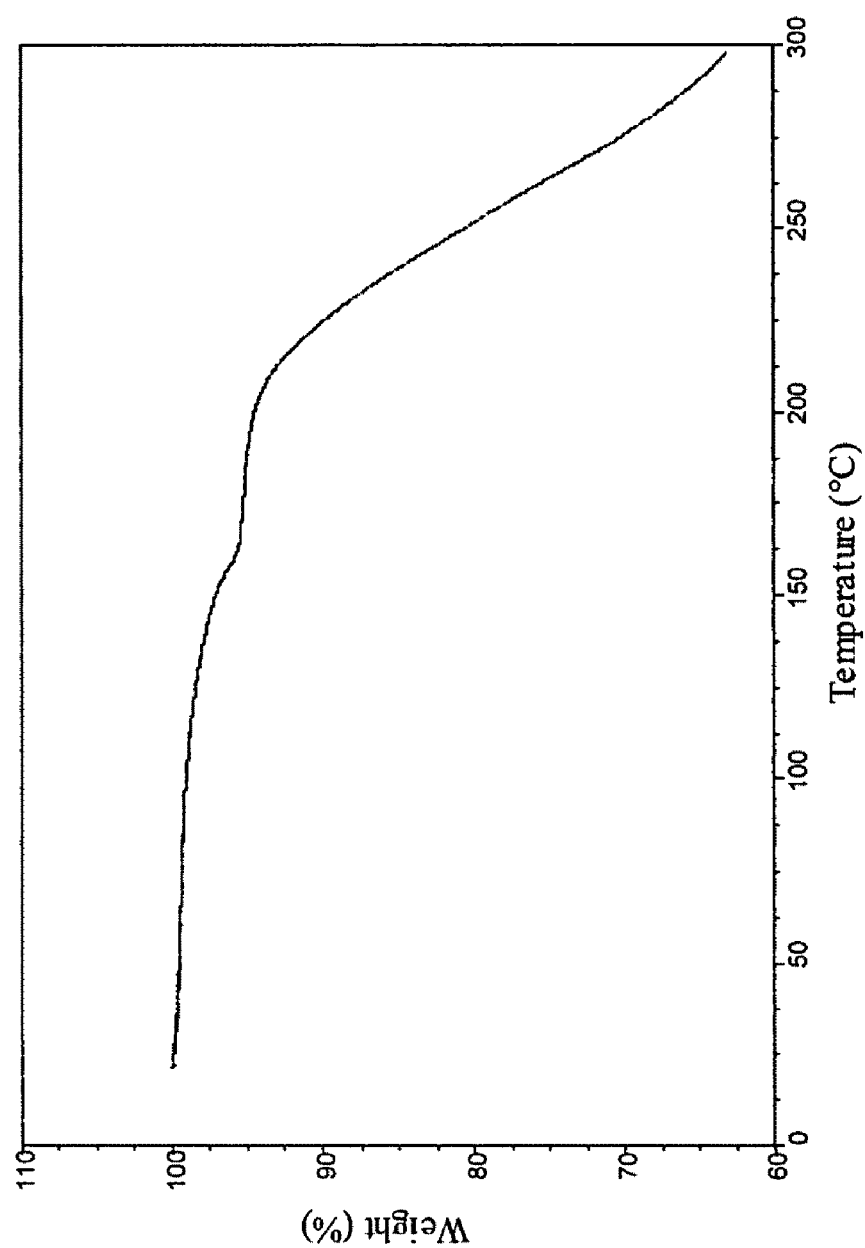
Figure 8:
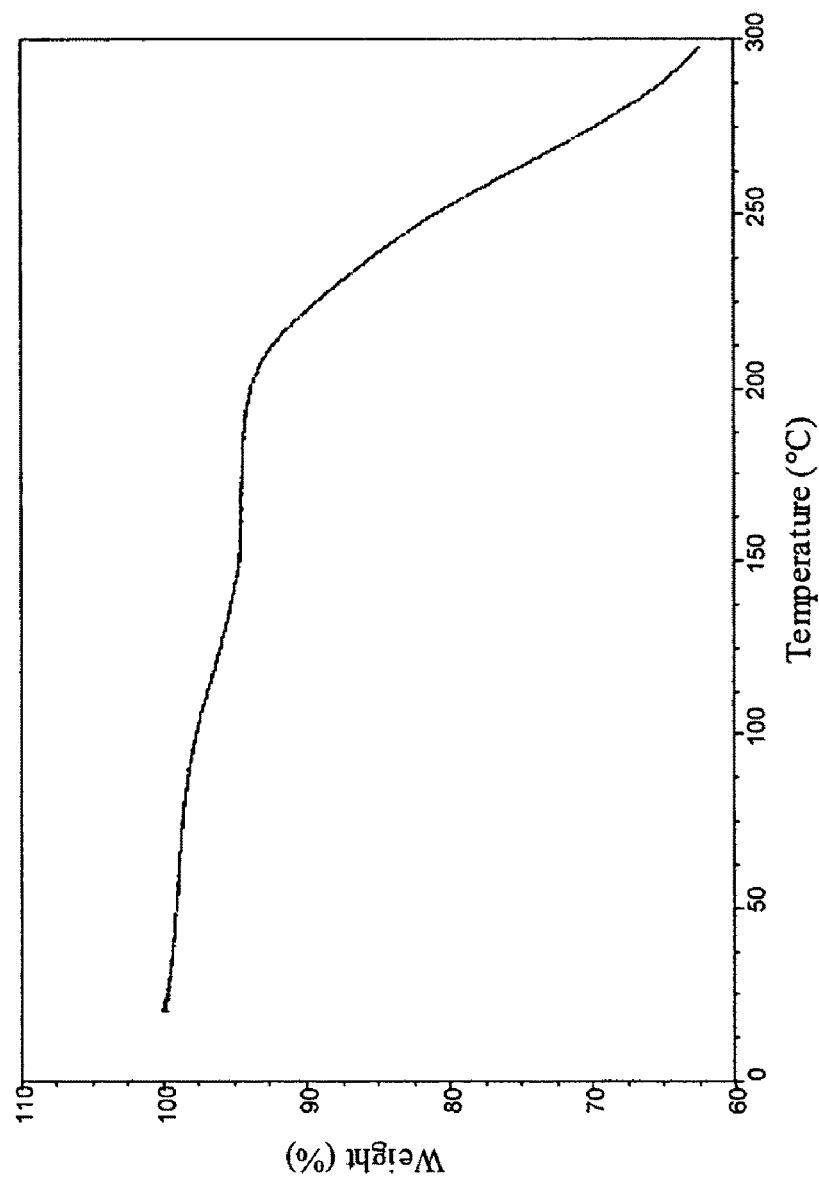
Figure 9:
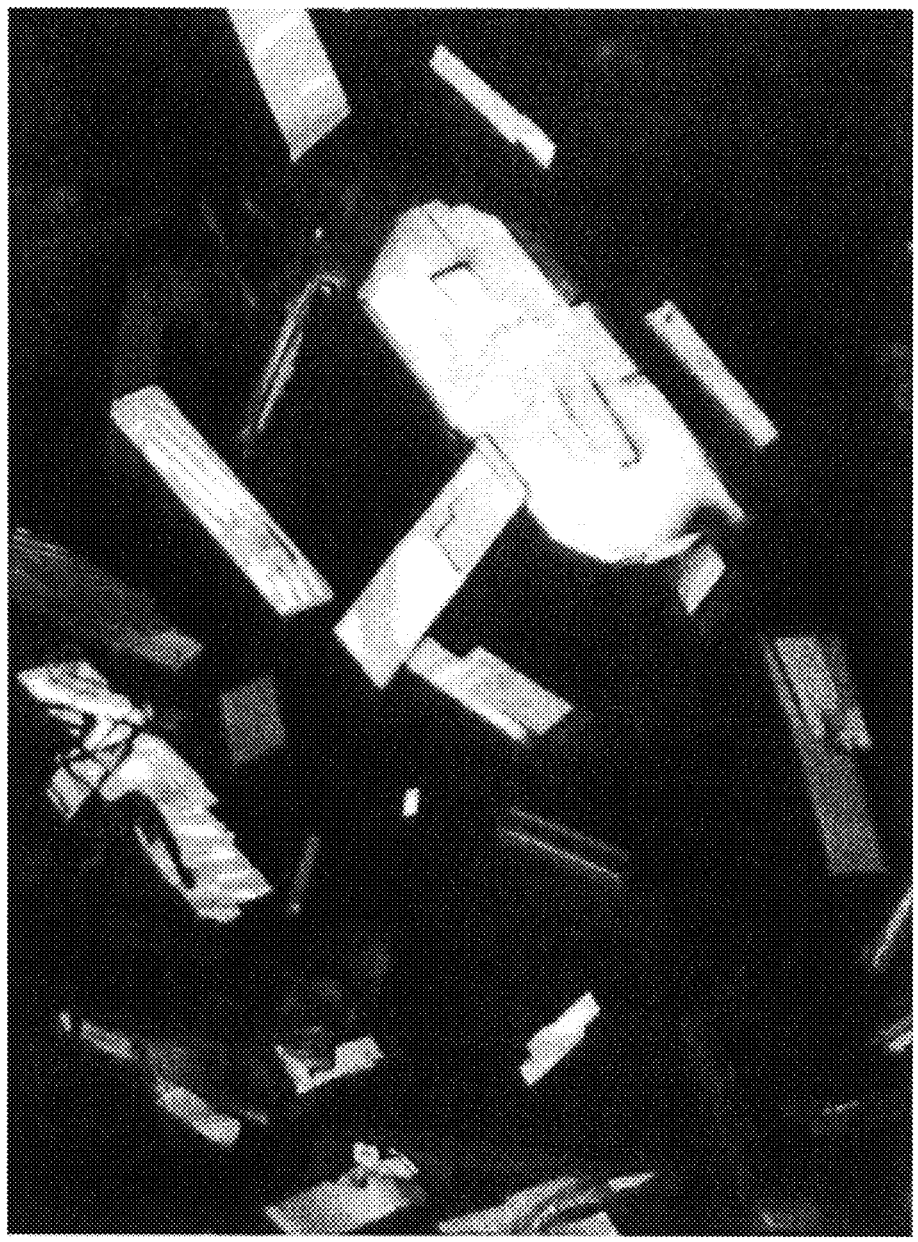
FIG. 9 is a polarized light micrographic image of this crystalline solvate.

In one embodiment, a crystalline heminapadisylate methanolate of the compound of formula I is characterized by a TGA trace which shows a loss of solvents and/or water (4.6%) at temperatures below about 165° C., as seen in FIG. 7. In one embodiment, a crystalline heminapadisylate ethanolate of the compound of formula I is characterized by a TGA trace which shows a loss of solvents and/or water (5.6%) at temperatures below about 160° C., as seen in FIG. 8.

In one embodiment, a crystalline heminapadisylate salt of the compound of formula I is characterized by a TGA trace which shows a loss of solvents and/or water (3.7%) at temperatures below about 170° C., as seen in FIG. 11.

Figure 18:
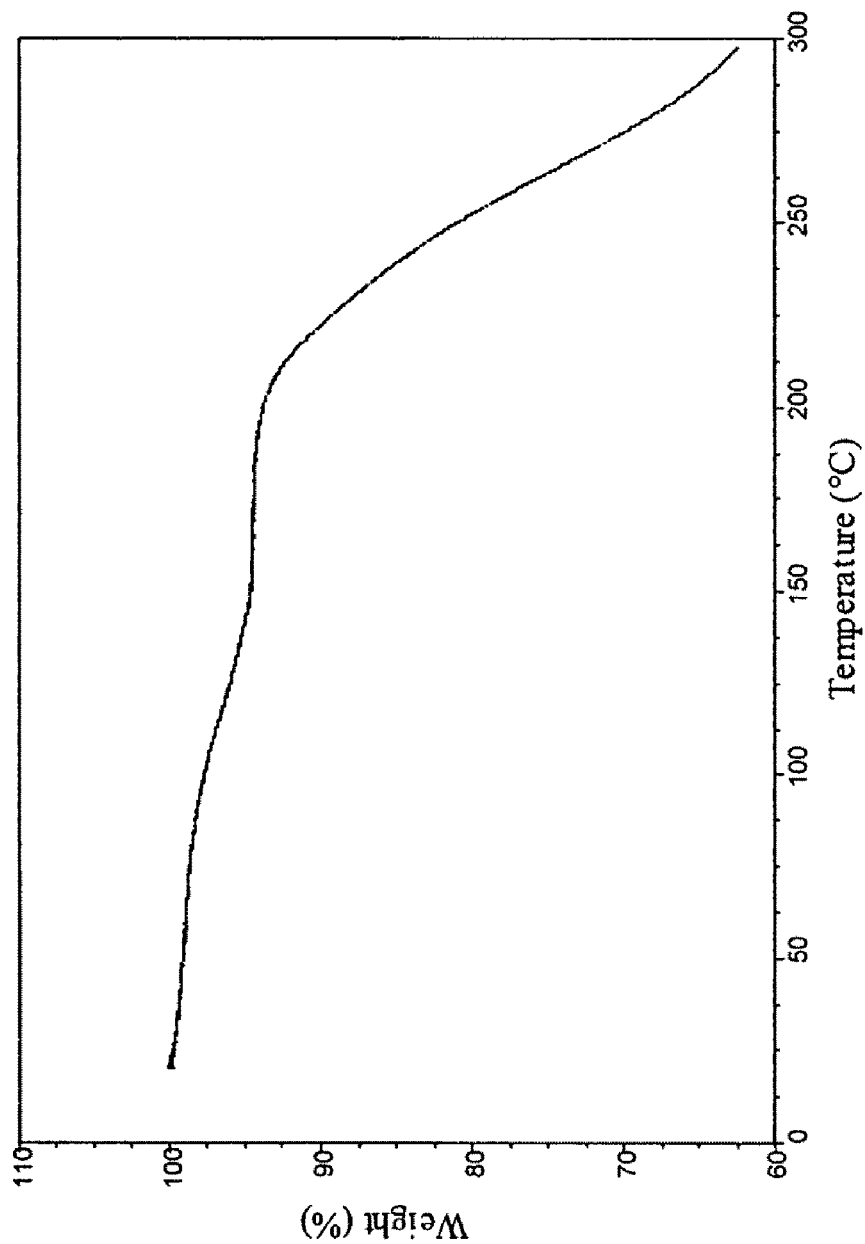

In one embodiment, a crystalline freebase (Form I) of the compound of formula I is characterized by a TGA trace which shows a loss of solvents and/or water (27%) at temperatures below about 85° C., as seen in FIG. 15. In one embodiment, a crystalline freebase (Form II) of the compound of formula I is characterized by a TGA trace which shows a loss of solvents and/or water (5.7%) at temperatures below about 94° C., as seen in FIG. 18.

The crystalline salts of the invention have been demonstrated to have a reversible sorption/desorption profile with acceptable levels of hygroscopicity. For example, a crystalline hemiedisylate salt of the compound of formula I has a moderate level of hygroscopicity, and has exhibited less than about 4% weight gain when exposed to up to 90% relative humidity, while a crystalline heminapadisylate salt has a low level of hygroscopicity, having demonstrated less than about 2% weight gain when exposed to up to 90% relative humidity.

Additionally, the crystalline compounds of the invention have been found to be stable upon exposure to elevated temperature and humidity. For example, after storage for 1 month at 40° C. and 75% relative humidity, analysis of a crystalline heminapadisylate salt by high performance liquid chromatography (HPLC) showed no detectable chemical degradation (i.e., less than 0.5% degradation for the neat crystalline salt).

These properties of the crystalline compounds of the invention are further illustrated in the Examples below.

Pharmaceutical Compositions and Formulations

The crystalline compound of formula I is typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. However, it will be understood by those skilled in the art that, once the crystalline salt of the invention has been formulated, it may no longer be in crystalline form, i.e., the salt may be dissolved in a suitable carrier.

Accordingly, in one embodiment, the invention is directed to a pharmaceutical composition comprising a pharmaceutically acceptable carrier or excipient and a crystalline biphenyl-2-ylcarbamic acid 1-[2-({3-[2-(4-hydroxybenzylamino)ethylcarbamoyl]benzoyl}methylamino)ethyl]piperidin-4-yl ester. The pharmaceutical composition may contain other therapeutic and/or formulating agents if desired.

The pharmaceutical compositions of the invention typically contain a therapeutically effective amount of a crystalline biphenyl-2-ylcarbamic acid 1-[2-({3-[2-(4-hydroxybenzylamino)ethylcarbamoyl]benzoyl}methylamino)ethyl]piperidin-4-yl ester, as the active agent. Typically, the pharmaceutical composition will contain from about 0.01 to 95% by weight of the active agent; including, from about 0.01 to 30% by weight; such as from about 0.01 to 10% by weight of the active agent.

Any conventional carrier or excipient may be used in the pharmaceutical compositions of the invention. The choice of a particular carrier or excipient, or combination of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials that can serve as pharmaceutically acceptable carriers include, but are not limited to, the following: sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; compressed propellant gases such as chlorofluorocarbons and hydrofluorocarbons; and other non-toxic compatible substances employed in pharmaceutical compositions.

The pharmaceutical compositions of the invention are typically prepared by thoroughly and intimately mixing or blending a crystalline compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of the invention are suitable for inhaled administration. Suitable pharmaceutical compositions for inhaled administration will typically be in the form of an aerosol or a powder. Such compositions are generally administered using well-known delivery devices such as a nebulizer inhaler, a metered-dose inhaler (MDI), a dry powder inhaler (DPI) or a similar delivery device.

In a specific embodiment of the invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Suitable nebulizer devices are commercially available, for example, by PARI GmbH (Starnberg, German). Other nebulizer devices include Respimat (Boehringer Ingelheim) and those described, for example, in U.S. Pat. No. 6,123,068 to Lloyd et al. and WO 97/12687 (Eicher et al.), the disclosures of which are incorporated herein by reference in their entirety.

A representative pharmaceutical composition for use in a nebulizer inhaler comprises an aqueous solution comprising from about 0.05 μg/mL to 10 mg/mL of a crystalline compound of formula I or a pharmaceutically acceptable solvate thereof. In one embodiment, the aqueous nebulizer formulation is isotonic. In one embodiment, the aqueous nebulizer formulation has a pH in the range of from about 4 to 6. In a particular embodiment, the aqueous nebulizer formulation is buffered with citrate buffer to a pH of about 4.5. In another particular embodiment, the aqueous nebulizer formulation comprises about 0.2 mg/mL free base equivalents of biphenyl-2-ylcarbamic acid 1-[2-({3-[2-(4-hydroxybenzylamino)ethylcarbamoyl]benzoyl}methylamino)ethyl]piperidin-4-yl ester.

In another specific embodiment of the invention, the pharmaceutical composition comprising the active agent is administered by inhalation using a DPI. Such DPIs typically administer the active agent as a free-flowing powder that is dispersed in a patient's air-stream during inspiration. In order to achieve a free flowing powder, the active agent is typically formulated with a suitable excipient such as lactose or starch. Micronization is a common method of reducing crystal size to that suitable for pulmonary delivery. Typically, the active agent is micronized and combined with a suitable carrier to form a suspension of micronized particles of respirable size, where "micronized particles" or "micronized form" means at least about 90% of the particles have a diameter of less than about 10 μm. Other methods of reducing particle size may also be used such as fine milling, chopping, crushing, grinding, milling, screening, trituration, pulverization, and so forth, as long as the desired particle size can be obtained.

A representative pharmaceutical composition for use in a DPI comprises dry lactose having a particle size between about 1 μm and 100 μm and micronized particles of a crystalline compound of formula I. Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of DPI delivery devices include Diskhaler (GlaxoSmithKline, Research Triangle Park, N.C.; see, e.g., U.S. Pat. No. 5,035,237 to Newell et al.); Diskus (GlaxoSmithKline; see, e.g., U.S. Pat. No. 6,378,519 to Davies et al.); Turbuhaler (AstraZeneca, Wilmington, Del.; see, e.g., U.S. Pat. No. 4,524,769 to Wetterlin); Rotahaler (GlaxoSmithKline; see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein. The disclosures of the aforementioned patents are incorporated herein by reference in their entirety.

In yet another specific embodiment of the invention, the pharmaceutical composition comprising the active agent is administered by inhalation using an MDI, which typically discharges a measured amount of the active agent using compressed propellant gas. Accordingly, pharmaceutical compositions administered using an MDI typically comprise a solution or suspension of the active agent in a liquefied propellant. Any suitable liquefied propellant may be employed including chlorofluorocarbons such as $CCl_3F$, and hydrofluoroalkanes (HFAs) such as 1,1,1,2-tetrafluoroethane (HFA 134a) and 1,1,1,2,3,3,3-heptafluoro-n-propane, (HFA 227ea). Due to concerns about chlorofluorocarbons affecting the ozone layer, formulations containing HFAs are generally preferred. Additional optional components of HFA formulations include co-solvents such as ethanol or pentane, and surfactants such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company), the disclosures of which are incorporated herein by reference in their entirety.

A representative pharmaceutical composition for use in an MDI comprises from about 0.01 to 5% by weight of a crystalline compound of formula I; from about 0 to 20% by weight ethanol; and from about 0 to 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of MDI devices developed specifically for use with HFA propellants are described in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.). The disclosures of the aforementioned patents and publications are incorporated herein by reference in their entirety.

For additional examples of processes of preparing respirable particles, and formulations and devices suitable for inhalation dosing see U.S. Pat. No. 6,268,533 to Gao et al.; U.S. Pat. No. 5,983,956 to Trofast; U.S. Pat. No. 5,874,063 to Briggner et al.; and U.S. Pat. No. 6,221,398 to Jakupovic et al.; and WO 99/55319 (Glaxo Group Ltd.) and WO 00/30614 (AstraZeneca AB); the disclosures of which are incorporated herein by reference in their entirety.

In another embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a salt of the invention as an active ingredient. The pharmaceutical composition may be packaged in a unit dosage form.

When intended for oral administration in a solid dosage form (i.e., as capsules, tablets, pills and the like), the pharmaceutical compositions of the invention will typically comprise a crystalline salt of the present invention as the active ingredient and one or more pharmaceutically acceptable carriers such as sodium citrate or dicalcium phosphate. Optionally or alternatively, such solid dosage forms may also comprise: fillers or extenders such as starches, lactose, sucrose, glucose, mannitol, and/or silicic acid; binders such as carboxymethylcellulose, alginates, gelatin, polyvinyl pyrrolidone, sucrose and/or acacia; humectants such as glycerol; disintegrating agents such as agar-agar, calcium carbonate, potato or tapioca starch, alginic acid, certain silicates, and/or sodium carbonate; solution retarding agents such as paraffin; absorption accelerators such as quaternary ammonium compounds; wetting agents such as cetyl alcohol and/or glycerol monostearate; absorbents such as kaolin and/or bentonite clay; lubricants such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically acceptable antioxidants include: water-soluble antioxidants such as ascorbic acid, cysteine hydrochloride, sodium bisulfate, sodium metabisulfate sodium sulfite and the like; oil-soluble antioxidants such as ascorbyl palmitate, butylated hydroxyanisole (BHA), butylated hydroxytoluene (BHT), lecithin, propyl gallate, alpha-tocopherol, and the like; and metal-chelating agents such as citric acid, ethylenediamine tetraacetic acid (EDTA), sorbitol, tartaric acid, phosphoric acid, and the like. Coating agents for tablets, capsules, pills and like, include those used for enteric coatings such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The crystalline compounds of the invention can also be administered transdermally using known transdermal delivery systems and excipients. For example, a compound of the invention can be admixed with permeation enhancers such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The crystalline compounds of the invention can also be co-administered with other therapeutic agents. This combination therapy involves using a compound of the invention combined with one or more of these secondary agents, either formulated together (e.g., packaged together in a single formulation) or formulated separately (e.g., packaged as separate unit dosage forms). Methods of formulating multiple agents together in the same formulation or in separate unit dosage forms, are well known in the art.

The additional therapeutic agent(s) can be selected from other bronchodilators (e.g., $PDE_3$ inhibitors, adenosine 2b modulators and $\beta_2$ adrenergic receptor agonists); anti-inflammatory agents (e.g., steroidal anti-inflammatory agents such as corticosteroids; non-steroidal anti-inflammatory agents (NSAIDs), and $PDE_4$ inhibitors); other muscarinic receptor antagonists (i.e., anticholinergic agents); antiinfective agents (e.g., Gram positive and Gram negative antibiotics or antivirals); antihistamines; protease inhibitors; and afferent blockers (e.g., $D_2$ agonists and neurokinin modulators).

One particular embodiment of the invention is directed to a composition comprising (a) a pharmaceutically acceptable carrier and a therapeutically effective amount of a crystalline form of the compound of formula I; and (b) a pharmaceutically acceptable carrier and a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the compound of formula I and the agent are formulated together or separately. In another embodiment, (b) is a pharmaceutically acceptable carrier and a therapeutically effective amount of a $\beta_2$ adrenergic receptor agonist and a steroidal anti-inflammatory agent. The secondary agents can be used in the form of pharmaceutically acceptable salts or solvates, and if appropriate, as optically pure stereoisomers.

Representative $\beta_2$ adrenergic receptor agonists that can be used in combination with crystalline compounds of the invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used include, but are not limited to, 3-(4-{[6-({(2R)-2-hydroxy-2-[4-hydroxy-3-(hydroxymethyl)phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds described in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)phenyl]imidazolidine-2,4-dione and related compounds described in WO 02/070490 (Glaxo Group Ltd.); 3-(4-{[6-({(2R)-2-[3-(formylamino)-4-hydroxyphenyl]-2-hydroxyethyl}amino) hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]oxy}butyl)benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino) hexyl]-oxy}butyl)benzenesulfonamide and related compounds described in WO 02/076933 (Glaxo Group Ltd.); 4-{(1R)-2-[(6-{2-[(2,6-dichlorobenzyl)oxy]ethoxy}hexyl) amino]-1-hydroxyethyl}-2-(hydroxymethyl)phenol and related compounds described in WO 03/024439 (Glaxo Group Ltd.); N-{2-[4-((R)-2-hydroxy-2-phenylethylamino) phenyl]ethyl}-(R)-2-hydroxy-2-(3-formamido-4-hydroxyphenyl)ethylamine and related compounds described in U.S. Pat. No. 6,576,793 to Moran et al.; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds described in U.S. Pat. No. 6,653,323 to Moran et al.; and pharmaceutically acceptable salts thereof. In a particular embodiment, the $\beta_2$-adrenoreceptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 µg to 500 µg per dose. The disclosures of the aforementioned patents and publications are incorporated herein by reference in their entirety.

Representative steroidal anti-inflammatory agents that can be used in combination with crystalline compounds of the invention include, but are not limited to, methyl prednisolone, prednisolone, dexamethasone, fluticasone propionate, 6α,9α-difluoro-17α-[(2-furanyl carbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl)ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the composition in a therapeutically effective amount. Typically, the steroidal anti-inflammatory agent will be present in an amount sufficient to provide from about 0.05 µg to 500 µg per dose.

An exemplary combination is a crystalline form of the compound of formula I, co-administered with salmeterol as the $\beta_2$ adrenergic receptor agonist, and fluticasone propionate as the steroidal anti-inflammatory agent. Another exemplary combination is a crystalline form of the compound of formula I, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl) ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent. As noted above, these agents can be formulated together or separately.

Other suitable combinations include, for example, other anti-inflammatory agents, e.g., NSATDs (e.g., sodium cromoglycate, nedocromil sodium, and phosphodiesterase (PDE) inhibitors such as theophylline, PDE4 inhibitors and mixed PDE3/PDE4 inhibitors); leukotriene antagonists (e.g., monteleukast); inhibitors of leukotriene synthesis; iNOS inhibitors; protease inhibitors such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

Representative phosphodiesterase-4 (PDE4) inhibitors or mixed PDE3/PDE4 inhibitors that can be used in combination with the crystalline compounds of the invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds described in WO99/16766 (Kyowa Hakko); K-34 (Kyowa Hakko); V-11294A (Napp); roflumilast (Byk-Gulden); pthalazinone compounds described in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with the crystalline compounds of the invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the crystalline compounds of the invention include, but are not limited to, ethanolamines such as carbinoxamine maleate, clemastine fumarate, diphenylhydramine hydrochloride and dimenhydrinate; ethylenediamines such as pyrilamine amleate, tripelennamine hydrochloride and tripelennamine citrate; alkylamines such as chlorpheniramine and acrivastine; piperazines such as hydroxyzine hydrochloride, hydroxyzine pamoate, cyclizine hydrochloride, cyclizine lactate, meclizine hydrochloride and cetirizine hydrochloride; piperidines such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Unless otherwise indicated, exemplary suitable doses for the other therapeutic agents administered in combination with a crystalline compound of the invention are in the range of about 0.05 µg/day to 100 mg/day.

The following formulations illustrate representative pharmaceutical compositions of the invention, as well as exemplary methods of preparation. One or more secondary agents can optionally be formulated with the crystalline compound of the invention (primary active agent). Alternately, the secondary agents(s) can be formulated separately and co-administered with the primary active agent, either simultaneously or sequentially. For example, in one embodiment, a single dry powder formulation can be manufactured to include both the crystalline compound of the invention and one or more secondary agents. In another embodiment, one formulation is manufactured to contain the crystalline compound of the invention and separate formulation(s) are manufactured to contain the secondary agent(s). Such dry powder formulations can then be packaged in separate blister packs and administered with a single DPI device.

Exemplary Dry Powder Formulation for Administration by Inhalation 0.2 mg of a crystalline compound of the invention is micronized and then blended with 25 mg of lactose. The blended mixture is then loaded into a gelatin inhalation cartridge. The contents of the cartridge are administered using a powder inhaler.

Exemplary Dry Powder Formulation for Administration by a Dry Powder Inhaler

A dry powder is prepared having a bulk formulation ratio of micronized crystalline compound of the invention (active agent) to lactose of 1:200. The powder is packed into a dry powder inhalation device capable of delivering between about 10 μg and 100 μg of active agent per dose.

Exemplary Formulations for Administration by a Metered Dose Inhaler

A suspension containing 5 wt % of a crystalline compound of the invention (active agent) and 0.1 wt % lecithin is prepared by dispersing 10 g of the active agent as micronized particles with a mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Alternately, a suspension containing 5 wt % of the active agent, 0.5 wt % lecithin, and 0.5 wt % trehalose is prepared by dispersing 5 g of the active agent as micronized particles with a mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Exemplary Aqueous Aerosol Formulation for Administration by Nebulizer

A pharmaceutical composition is prepared by dissolving 0.5 mg of a crystalline compound of the invention (active agent) in 1 mL of a 0.9% sodium chloride solution acidified with citric acid. The mixture is stirred and sonicated until the active agent is dissolved. The pH of the solution is adjusted to a value in the range of from 3 to 8 (typically about 5) by the slow addition of NaOH.

Exemplary Hard Gelatin Capsule Formulation for Oral Administration

The following ingredients are thoroughly blended and then loaded into a hard gelatin capsule: 250 mg of a crystalline compound of the invention, 200 mg of lactose (spray-dried), and 10 mg of magnesium stearate, for a total of 460 mg of composition per capsule.

Exemplary Suspension Formulation for Oral Administration

The following ingredients are mixed to form a suspension containing 100 mg of active ingredient per 10 mL of suspension.

| Ingredients | Amount |
| --- | --- |
| Crystalline compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Exemplary Injectable Formulation

The following ingredients are blended and the pH is adjusted to 4±0.5 using 0.5 N HCl or 0.5 N NaOH.

| Ingredients | Amount |
| --- | --- |
| Crystalline compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Utility

The compound of formula I possesses muscarinic receptor antagonist activity and therefore, the crystalline form of the compound of formula I or solvates thereof, are expected to be useful for treating medical conditions mediated by muscarinic receptors, i.e., medical conditions which are ameliorated by treatment with a muscarinic receptor antagonist. Such medical conditions include, by way of example, pulmonary disorders or diseases including those associated with reversible airway obstruction such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders such as overactive bladder or detrusor hyperactivity and their symptoms; gastrointestinal tract disorders such as irritable bowel syndrome, diverticular disease, achalasia, gastrointestinal hypermotility disorders and diarrhea; cardiac arrhythmias such as sinus bradycardia; Parkinson's disease; cognitive disorders such as Alzheimer's disease; dismenorrhea; and the like.

Accordingly, in one embodiment, the invention is directed to a method for treating a pulmonary disorder, comprising administering to a patient a therapeutically effective amount of a crystalline biphenyl-2-ylcarbamic acid 1-[2-({3-[2-(4-hydroxybenzylamino)ethylcarbamoyl]benzoyl}methylamino)ethyl]piperidin-4-yl ester. When used to treat a pulmonary disorder, the crystalline compound of the invention will typically be administered by inhalation in multiple doses per day, in a single daily dose or a single weekly dose. Generally, the dose for treating a pulmonary disorder will range from about 10 μg/day to 200 μg/day.

When administered by inhalation, the crystalline compounds of the invention typically have the effect of producing bronchodilation. Accordingly, in another embodiment, the invention is directed to a method of producing bronchodilation in a patient, comprising administering to a patient a bronchodilation-producing amount of a crystalline biphenyl-2-ylcarbamic acid 1-[2-({3-[2-(4-hydroxybenzylamino)ethylcarbamoyl]benzoyl}methylamino)ethyl]piperidin-4-yl ester. Generally, the therapeutically effective dose for producing bronchodilation will range from about 10 µg/day to 200 µg/day.

In one embodiment, the invention is directed to a method of treating chronic obstructive pulmonary disease or asthma, comprising administering to a patient a therapeutically effective amount of a crystalline biphenyl-2-ylcarbamic acid 1-[2-({3-[2-(4-hydroxybenzylamino)ethylcarbamoyl]benzoyl}methylamino)ethyl]piperidin-4-yl ester. When used to treat a COPD or asthma, the crystalline compound of the invention will typically be administered by inhalation in multiple doses per day or in a single daily dose. Generally, the dose for treating COPD or asthma will range from about 10 µg/day to 200 µg/day. As used herein, COPD includes chronic obstructive bronchitis and emphysema (see, for example, Barnes, Chronic Obstructive Pulmonary Disease, *N Engl J Med* 343:269-78 (2000)).

When used to treat a pulmonary disorder, the crystalline compounds of the invention are optionally administered in combination with other therapeutic agents. Accordingly, in a particular embodiment, the pharmaceutical compositions and methods of the invention further comprise a therapeutically effective amount of a $\beta_2$-adrenoreceptor agonist, a corticosteroid, a non-steroidal anti-inflammatory agent, or combination thereof.

In another embodiment, the crystalline compounds of the invention are used to antagonize a muscarinic receptor in a biological system, and a mammal in particular such as mice, rats, guinea pigs, rabbits, dogs, pigs, humans and so forth. In this embodiment, a therapeutically effective amount of a crystalline biphenyl-2-ylcarbamic acid 1-[2-({3-[2-(4-hydroxybenzylamino)ethylcarbamoyl]benzoyl}methylamino)ethyl]piperidin-4-yl ester, is administered to the mammal. If desired, the effects of antagonizing the muscarinic receptor can then be determined using conventional procedures and equipment.

The properties and utility of the crystalline compounds of the invention can be demonstrated using various in vitro and in vivo assays that are well-known to those skilled in the art. For example, representative assays are described in further detail in the following Examples.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:

AC adenylyl cyclase
ACh acetylcholine
ACN acetonitrile
BSA bovine serum albumin
cAMP 3'-5' cyclic adenosine monophosphate
CHO Chinese hamster ovary
cM5 cloned chimpanzee M5 receptor
DCM dichloromethane (i.e., methylene chloride)
DIPEA N,N-diisopropylethylamine
DMF N,N-dimethylformamide
DMSO dimethyl sulfoxide
dPBS Dulbecco's phosphate buffered saline
EDCI 1-(3-dimethylaminopropyl)-3-ethylcarbodiimide hydrochloride
EDTA ethylenediaminetetraacetic acid
EtOAc ethyl acetate
EtOH ethanol
FBS fetal bovine serum
FLIPR fluorometric imaging plate reader
HATU O-(7-azabenzotriazol-1-yl-N,N,N',N'-tetramethyluronium hexafluorophosphate
HBSS Hank's buffered salt solution
HEPES 4-(2-hydroxyethyl)-1-piperazineethanesulfonic acid
$hM_1$ cloned human M1 receptor
$hM_2$ cloned human M2 receptor
$hM_3$ cloned human M3 receptor
$hM_4$ cloned human M4 receptor
$hM_5$ cloned human M5 receptor
HOAc acetic acid
HOBT 1-hydroxybenzotriazole hydrate
HPLC high-performance liquid chromatography
IPA isopropanol
LCMS liquid chromatography mass spectrometry
MCh methylcholine
MeOH methanol
MTBE methyl f-butyl ether
$NaBH(OAc)_3$ sodium triacetoxyborohydride
TFA trifluoroacetic acid
THF tetrahydrofuran Any other abbreviations used herein but not defined have their standard, generally accepted meaning. Unless noted otherwise, reagents, starting materials and solvents were purchased from commercial suppliers (such as Sigma-Aldrich, Fluka, and the like) and were used without further purification.

Unless otherwise indicated, HPLC analysis was conducted using an Agilent (Palo Alto, Calif.) Series 1100 instrument equipped with Zorbax Bonus RP 2.1×50 mm columns (Agilent) having a 3.5 micron particle size. Detection was by UV absorbance at 214 nm. The mobile phases employed were as follows (by volume): A is ACN (2%), water (98%) and TFA (0.1%); and B is ACN (90%), water (10%) and TFA (0.1%). HPLC 10-70 data was obtained using a flow rate of 0.5 mL/minute of 10 to 70% B over a 6 minute gradient (with the remainder being A). Similarly, HPLC 5-35 data and HPLC 10-90 data were obtained using 5 to 35% B; or 10 to 90% B over a 5 minute gradient.

LCMS data were obtained with an Applied Biosystems (Foster City, Calif.) Model API-150EX instrument. LCMS 10-90 data was obtained using 10 to 90% Mobile Phase B over a 5 minute gradient.

Small-scale purification was conducted using an API-150EX Prep Workstation system from Applied Biosystems. The mobile phases employed were as follows (by volume): A is water and 0.05% TFA; and B is ACN and 0.05% TFA. For arrays (typically about 3 to 50 mg recovered sample size), the following conditions were used: 20 mL/min flow rate; 15 minute gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 minute gradients and a 41.4 mm×250 mm Microsorb BDS column with 10 micron particles (Varian, Palo Alto, Calif.).

Preparation 1

N-(2-tert-Butoxycarbonylaminoethyl)isophthalamic Acid Methyl Ester

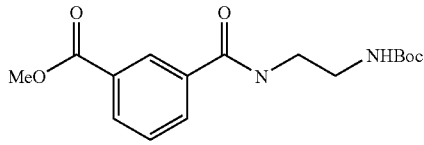

Mono-methyl isophthalate (10.0 g, 55.5 mmol), t-butyl n-(2-aminoethyl)carbamate (8.89 g, 55.5 mmol, 1.0 eq) and EDCI (12.2 g, 63.8 mmol, 1.15 eq) were dissolved in 270 mL DCM, followed by the addition of DIPEA (29.0 mL, 166 mmol, 3.0 eq). The reaction was allowed to stir at room temperature overnight. It was then taken up in 100 mL of DCM, washed with a 1:1 solution of 1.0 N HCl in brine, water, and a 1:1 solution of brine in saturated NaHCO$_3$. The organic layer was dried over Na$_2$SO$_4$, filtered and concentrated to afford the product as a light yellow solid (12.81 g, 72%).

Preparation 2

N-(2-tert-Butoxycarbonylaminoethyl)isophthalamic Acid

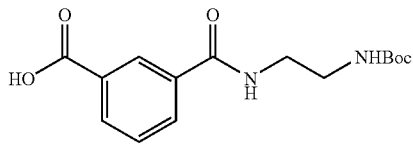

38.8 g of N-(2-tert-butoxycarbonylaminoethyl)isophthalamic acid methyl ester (prepared as described in Preparation 1) was dissolved in a solution of THF/DMF (1:1, 740 mL), and NaOH (111 mL of 10 N solution, 1.11 mol, 10.0 eq) was added. The reaction was stirred at room temperature overnight. The pH was then adjusted to pH 9 using 1.0 N HCl and concentrated to ~250 mL volume under vacuum. The mixture was filtered to remove impurities. The filtrate was further acidified to pH 5 by slow addition of 1.0 N HCl, and concentrated to ~200 mL volume. The precipitate was collected by filtration, rinsed with water and EtOAc, and dried under vacuum to give the product as a white solid (17.75 g, 52%).

For large scale synthesis, the reaction was carried out in MTBE using 2N NaOH (3 eq). The title compound was further purified via crystallization in MeOH.

Preparation 3

Biphenyl-2-ylcarbamic Acid Piperidin-4-yl Ester

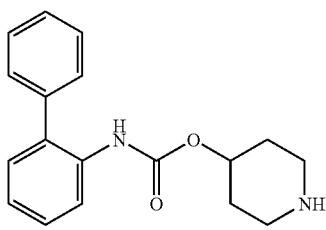

Biphenyl-2-isocyanate (97.5 g, 521 mmol) and 4-hydroxy-N-benzylpiperidine (105 g, 549 mmol) were heated together at 70° C. for 12 hours. The reaction mixture was then cooled to 50° C., EtOH (1 L) was added and then 6M HCl (191 mL) was added slowly. The resulting mixture was then cooled to ambient temperature, ammonium formate (98.5 g, 1.56 mol) was added, and then nitrogen gas was bubbled through the solution vigorously for 20 minutes. Palladium on activated carbon (20 g, 10 wt % dry basis) was added and the reaction mixture was heated at 40° C. for 12 hours, and then filtered through a pad of Celite. The solvent was then removed under reduced pressure and 1M HCl (40 mL) was added to the crude residue. The pH of the mixture was then adjusted with 10N NaOH to pH 12. The aqueous layer was extracted with EtOAc (2×150 mL) and the organic layer was dried (magnesium sulfate), filtered and the solvent removed under reduced pressure to give 155 g of the title intermediate (100% yield). HPLC (10-70) R$_t$=2.52; m/z: [M+H]$^+$ calcd for C$_{18}$H$_{20}$N$_2$O$_2$, 297.15; found, 297.3.

Preparation 4

N-Benzyl-N-methylaminoacetaldehyde

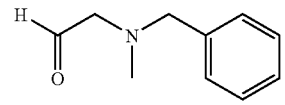

To a 3-necked 2-L flask was added N-benzyl-N-methylethanolamine (30.5 g, 0.182 mol), DCM (0.5 L), DIPEA (95 mL, 0.546 mol) and DMSO (41 mL, 0.728 mol). Using an ice bath, the mixture was cooled to about −10° C. and sulfur trioxide pyridine-complex (87 g, 0.546 mol) was added in 4 portions over 5 minute intervals. The reaction was stirred at −10° C. for 2 hours. Before removing the ice-bath, the reaction was quenched by adding water (0.5 L). The aqueous layer was separated and the organic layer was washed with water (0.5 L) and brine (0.5 L) and then dried over magnesium sulfate and filtered to provide the title compound which was used without further purification.

Preparation 5

Biphenyl-2-ylcarbamic Acid 1-[2-(Benzylmethylamino)ethyl]piperidin-4-yl Ester

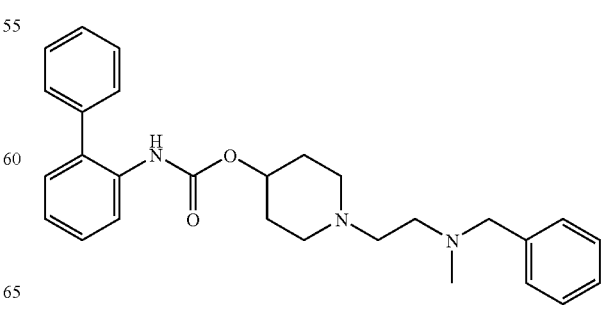

To a 2-L flask, containing N-benzyl-N-methylaminoacetaldehyde in DCM (0.5 L; prepared as described in Preparation 4) was added biphenyl-2-ylcarbamic acid piperidin-4-yl ester (30 g, 0.101 mol; prepared as described in Preparation 3) followed by NaBH(OAc)$_3$ (45 g, 0.202 mol). The reaction mixture was stirred overnight and then quenched by the addition of 1 N HCl (0.5 L) with vigorous stirring. Three layers were observed and the aqueous layer was removed. After washing with 1N NaOH (0.5 L), a homogenous organic layer was obtained which was then washed with a saturated solution of aqueous NaCl (0.5 L), dried over magnesium sulfate, filtered and the solvent removed under reduced pressure. The residue was purified by dissolving it in a minimal amount of isopropanol and cooling this solution to 0° C. to form a solid which was collected and washed with cool isopropanol to provide 42.6 g of the title compound (95% yield). MS m/z: [M+H$^+$] calcd for $C_{28}H_{33}N_3O_2$, 444.3; found, 444.6. $R_f$=3.51 min (10-70 ACN:H$_2$O, reverse phase HPLC).

Preparation 5A

Alternately, the title compound was prepared by mesylation of N-benzyl-N-methyl ethanolamine, which was then reacted with biphenyl-2-ylcarbamic acid piperidin-4-yl ester in an alkylation reaction.

A 500 mL flask (reactor flask) was charged with N-benzyl-N-methylethanolamine (24.5 mL), DCM (120 mL), NaOH (80 mL; 30 wt %) and tetrabutylammonium chloride. Mixing at low speed throughout the reaction, the mixture was cooled to −10° C. (cooling bath), and the addition funnel charged with DCM (30 mL) and mesyl chloride (15.85 mL), which was added drop wise at a constant rate over 30 minutes. The addition was exothermic, and stirring was continued for 15 minutes while the temperature equilibrated back to −10° C. The reaction was held for at least 10 minutes to ensure full hydrolysis of the excess mesyl chloride.

A 250 mL flask was charged with biphenyl-2-ylcarbamic acid piperidin-4-yl ester (26 g; prepared as described in Preparation 3) and DCM (125 mL), stirred for 15 minutes at room temperature, and the mixture chilled briefly to 10° C. to form a slurry. The slurry was then charged into the reactor flask via the addition funnel. The cooling bath was removed and the reaction mixture was warmed to 5° C. The mixture was transferred to a separatory funnel, the layers allowed to settle, and the aqueous layer removed. The organic layer was transferred back to the reactor flask, stirring resumed, the mixture held to room temperature, and the reaction monitored by HPLC for a total of 3.5 hours.

The reactor flask was charged with NaOH (1M solution; 100 mL), stirred, and the layers allowed to settle. The organic layer was separated, washed (NaCl saturated solution), its volume partially reduced under vacuum, and subjected to repeated IPA washings. The solids were collected and allowed to air-dry (25.85 g, 98% purity). Additional solids were obtained from further processing of the mother liquor (volume reduction, IPA, cooling).

Preparation 6

Biphenyl-2-ylcarbamic Acid
1-(2-Methylaminoethyl)piperidin-4-yl Ester

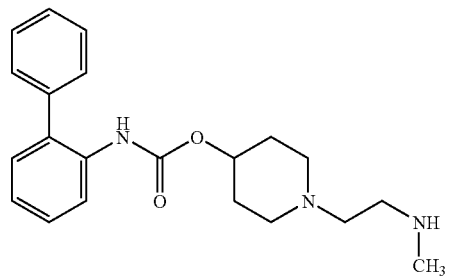

To a Parr hydrogenation flask was added biphenyl-2-ylcarbamic acid 1-[2-(benzylmethylamino)ethyl]piperidin-4-yl ester (40 g, 0.09 mol; prepared as described in Preparation 5) and EtOH (0.5 L). The flask was flushed with nitrogen gas and palladium on activated carbon (15 g, 10 wt % dry basis, 37% wt/wt) was added along with HOAc (20 mL). The mixture was kept on the Parr hydrogenator under a hydrogen atmosphere (~50 psi) for 3 hours. The mixture was then filtered and washed with EtOH. The filtrate was condensed and the residue was dissolved in a minimal amount of DCM. Isopropyl acetate (10 volumes) was added slowly to form a solid which was collected to provide 22.0 g of the title compound (70% yield). MS m/z: [M+H$^+$] calcd for $C_{21}H_{27}N_3O_2$, 354.2; found, 354.3. $R_f$=2.96 min (10-70 ACN:H$_2$O, reverse phase HPLC).

Preparation 7

Biphenyl-2-ylcarbamic acid 1-(2-}[3-(2-tert-butoxycarbonylaminoethylcarbamoyl)benzoyl]methylamino}ethyl)piperidin-4-yl ester

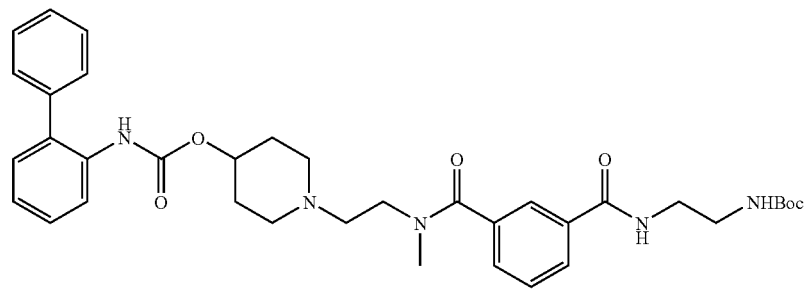

To a solution of N-(2-tert-butoxycarbonylaminoethyl) isophthalamic acid (9.35 g, 30.3 mmol; prepared as described in Preparation 2) and biphenyl-2-ylcarbamic acid 1-(2-methylaminoethyl)piperidin-4-yl ester (9.64 g, 27.3 mmol, 0.9 eq; prepared as described in Preparation 6) in 150 mL of DCM was added EDCI (6.98 g, 36.4 mmol, 1.2 eq) followed by 15.8 mL of DIPEA (91.0 mmol, 3.0 eq). At this point, HPLC analysis was conducted to ascertain the extent of reaction. Following overnight stirring, the reaction was concentrated under vacuum and taken up in 200 mL DCM. The mixture was then washed twice with 150 mL aqueous saturated NaHCO$_3$, once with 150 mL brine and 5 times with 200 mL of a 1:1 solution of 1.0 N HCl in brine to remove any residual ester. The organic phase was then dried over Na$_2$SO$_4$, filtered and concentrated. 20.15 g of crude product was obtained as a white foam solid and used in the next step without further purification.

For large scale synthesis, the reaction was carried out in DCM in the presence of EDCI (1.2 eq), HOBT (1.2 eq) and DIPEA (3 eq) for 16 hours at room temperature and 5 hours at reflux.

Preparation 7A

Alternately, the title compound was prepared by acylation of 3-acetylbenzoic acid with biphenyl-2-ylcarbamic acid 1-(2-methylaminoethyl)piperidin-4-yl ester, which then underwent oxidation, followed by an N-acylation step.

3-carboxybenzaldehyde (4.07 g, 27.11 mmol, 1 eq), HATU (10.307 g, 27.11 mmol, 1 eq) and biphenyl-2-ylcarbamic acid 1-(2-methylaminoethyl)piperidin-4-yl ester (9.58 g, 27.11 mmol, 1 eq; prepared as described in Preparation 6) were dissolved in a solution of DCM (100 mL) and DMF (10 mL). DIPEA (14 mL, 81.33 mmol, 3 eq) was added portionwise and the solution was allowed to stir at room temperature. The reaction mixture was concentrated under vacuum, yielding a yellow oil (34.1 g). The crude oil was dissolved in DCM and washed with H$_2$O:brine (3×, 200 mL) and with brine (1×). The organic layer was concentrated under vacuum to afford biphenyl-2-ylcarbamic acid 1-{2-[(3-formylbenzoyl)methylamino]ethyl}piperidin-4-yl ester as a yellow foam (13.165 g, 98%):

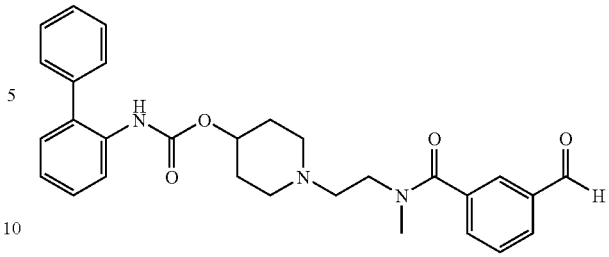

This aldehyde was oxidized to N-{2-[4-(biphenyl-2-ylcarbamoyloxy)piperidin-1-yl]ethyl}-N-methylisophthalamic acid using sulfamic acid (3.95 g, 40.65 mmol, 1.5 eq) and NaClCO$_2$ (4.6 g, 40.65 mmol, 1.5 eq, dissolved in 20 mL of H$_2$O) in glacial acetic acid (35 mL) at 0° C. for 40 minutes and at room temperature for 1 hour. After workup, the crude acid was obtained as an orange semi-solid (18.51 g):

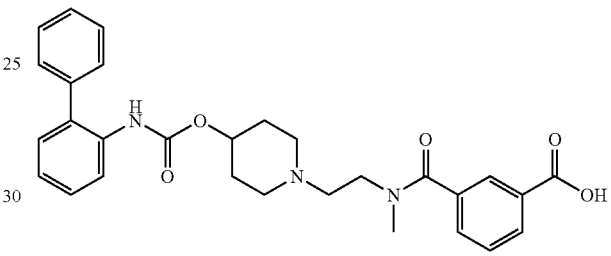

This acid was then coupled with t-butyl n-(2-aminoethyl) carbamate to yield the title compound.

Preparation 8

Biphenyl-2-ylcarbamic Acid 1-(2-{[3-(2-Aminoethylcarbamoyl)benzoyl]methylamino}ethyl)piperidin-4-yl Ester

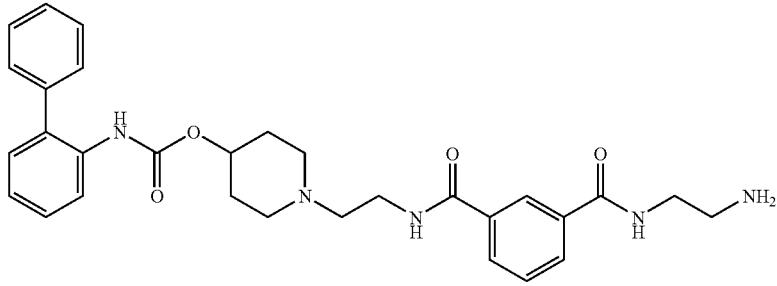

To a solution of the product of Preparation 7 (20.15 g) in 20 mL DCM was added 30 mL TFA in 40 mL DCM. The reaction was stirred at room temperature for 1 hour, followed by concentration under high vacuum using toluene for azeotroph. The crude product was taken up in 200 mL DCM and washed twice with 200 mL solutions of 1:1 brine and 1.0 N NaOH. Additional 1.0 N NaOH was added to achieve a pH of 10. The organic phase was lastly washed with 200 mL brine, dried over Na$_2$SO$_4$, filtered and concentrated. 16.8 g of the title compound was obtained as an off-white solid in 98% yield.

Example 1

Biphenyl-2-ylcarbamic Acid 1-[2-({3-[2-(4-Hydroxybenzylamino)ethylcarbamoyl]benzoyl}methylamino)ethyl]piperidin-4-yl Ester

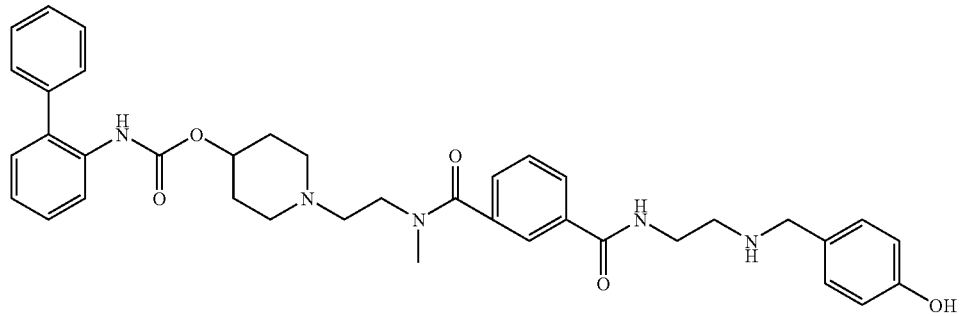

A solution of biphenyl-2-ylcarbamic acid 1-(2-{[3-(2-aminoethylcarbamoyl)benzoyl]methylamino}ethyl)piperidin-4-yl ester (9.31 g, 17.1 mmol; prepared as described in Preparation 8) and 4-hydroxybenzaldehyde (2.30 g, 18.8 mmol, 1.1 eq) in 125 mL MeOH was stirred at room temperature for 2 hours. NaBH(OAc)$_3$ (7.26 g, 34.2 mmol, 2.0 eq) was added to the reaction at room temperature in two portions separated in one hour interval. The reaction was stirred for an additional hour before being concentrated under vacuum. The residue was taken up in 100 mL DCM and stirred with 100 mL of 1.0 N HCl for 1 hour. The aqueous phase was adjusted to pH 9 using 10.0 N NaOH. The mixture was stirred for an additional 10 minutes. The organic phase was separated, dried over Na$_2$SO$_4$, filtered and concentrated under vacuum. The crude material was purified using silica gel chromatography (7% MeOH in CH$_2$Cl$_2$ with 1% NH$_4$OH as eluent). The title compound was obtained as an off-white solid (8.08 g, 73%). MS m/z: [M+H$^+$] calcd for C$_{38}$H$_{43}$N$_5$O$_5$, 650.34; found, 650.2.

The title compound was also prepared as the diacetate salt. The freebase (1.004 g, 1.538 mmol) was dissolved in 2 mL of MeOH/ACN (1:1). The solution was sonicated and heated until completely clear. To the clear solution was added HOAc (174 μL, 3.06 mmol) and mixed thoroughly with vortex action. Additional ACN (~10 mL) was added drop-wise until the solution turned cloudy. The resulting solution was heated until clear and allowed to sit at room temperature overnight to form white crystalline material. The solid was filtered, washed with ACN (3×10 mL) and dried under vacuum to give the diacetate salt as a white crystalline solid (900 mg, 76%). The diacetate salt can then be used to provide a further purified freebase by a two-step reaction with saturated NH$_4$HCO$_3$ and MeOH. Crude free base having 91% purity was treated with HOAc and MeOH/ACN to yield a diacetate salt having approximately 97% purity, which was then treated with saturated NH$_4$HCO$_3$ and MeOH to yield a pure free base having 98+% purity.

The title compound was also prepared as the mono-oxalate salt. The freebase (1 g, 1.54 mmol) was dissolved in 1 mL of MeOH/ACN (1:1). The solution was sonicated until completely clear. To the solution was added oxalic acid in EtOH (1M, 1.54 mL, 1 eq) followed by ACN until the solution became cloudy (~8 mL). The cloudy solution was stirred at 50° C. for 1.5 hours and slowly cooled to room temperature under stirring. The solid was filtered, washed with ACN (5 mL×3) and dried under high vacuum to give the mono-oxalate salt as a white crystalline solid (0.8 g, 70%).

The title compound was also prepared as the dipropionate salt. The freebase (107 mg, 0.165 mmol) was dissolved in 4 mL of ACN. The solution was sonicated and heated until completely clear. Propionic acid (25 μL, 0.33 mmol) was added to the solution and the solution turned cloudy. MeOH (50 mL) was added in and the solution was stirred at 50° C. until it was completely clear. The solution was slowly cooled down to room temperature and stirred overnight to form a white crystalline material. The solid was filtered, washed with ACN (0.5 mL×3) and dried under vacuum to give the dipropionate salt as a white crystalline solid (82.3 mg, 63%).

Example 2

Crystalline Hemiedisylate Salt of Biphenyl-2-ylcarbamic Acid 1-[2-({3-[2-(4-Hydroxybenzylamino)ethylcarbamoyl]benzoyl}methylamino)ethyl]piperidin-4-yl Ester Biphenyl-2-ylcarbamic acid 1-[2-({3-[2-(4-hydroxybenzylamino)ethylcarbamoyl]benzoyl}methylamino)ethyl]piperidin-4-yl ester (1.07 g, 1.66 mmol amorphous freebase; prepared as described in Example 1) was dissolved in a round bottom flask in a solvent mixture of 20% MeOH and 80% ACN (10 mL). A free acid solution of 1,2 ethane disulfonic acid (½ mole equivalent of acid, 0.19 g, 0.83 mmol) was dissolved in the same solvent system (20% MeOH, 80% ACN, 1 mL). The acid solution was added drop wise to the freebase solution over 10 minutes, while stirring at approximately 22° C. Once the acid was completely fed to the flask, the liquor appeared cloudy-white. The liquor was heated to 50° C. for one-half hour, then slowly cooled to 22° C. Agitation was continued for 2 hours to enable greater recovery and growth of the crystals. The crystals were recovered from the slurry by vacuum filtration, and the cake was washed with ACN (1 mL×3), followed by vacuum drying. The yield was 87.6% (99.4% purity) with respect to the freebase starting material. HPLC, XRPD, NMR and ion analysis confirmed this was a crystalline hemiedisylate salt.

Example 3

Crystalline Heminapadisylate Methanolate of Biphenyl-2-ylcarbamic Acid 1-[2-({3-[2-(4-Hydroxybenzylamino)ethylcarbamoyl]benzoyl}methylamino)ethyl]piperidin-4-yl Ester Biphenyl-2-ylcarbamic acid 1-[2-({3-[2-(4-hydroxybenzylamino)ethylcarbamoyl]benzoyl}methylamino)ethyl]piperidin-4-yl ester (18.87 g, 29.04 mmol, 98.57% pure amorphous freebase; prepared as described in Example 1) was dissolved in a solvent mixture of 20% MeOH and 80% ACN (250 mL). Naphthalene-1,5-disulfonic acid (½ mole equivalent, 4.573 g, 3.97 mmol) was dissolved in 170 mL of equivalent solvent mixture. The acid went into solution after vigorous sonication (heating could alternately be used to speed dissolution of the acid). The overall salt mass to solvent volume ratio was 1:18. The freebase solution was placed in round bottom flask, in a large oil bath. To the freebase solution, the acid solution was added drop wise via an addition funnel, while stirring at room temperature. The acid feed rate was approximately 5 mL per minute. After adding approximately 75 mL of the acid solution the reaction mixture was heated to 30° C. The mixture became partially cloudy at this temperature. After addition of the 170 mL of acid, the solution was heated to 50° C. The mixture was stirred at 50° C. for one-half hour before it was slowly cooled to room temperature, while stirring over night. Over this period, crystallization occurred. The solid was filtered, washed with a solvent mixture containing 10% MeOH/90% ACN (100 mL×3) and a yield of 84% (99.0% purity) was obtained (freebase equivalent).

Example 4

Crystalline Heminapadisylate Ethanolate of Biphenyl-2-ylcarbamic Acid 1-[2-({3-[2-(4-Hydroxybenzylamino)ethylcarbamoyl]benzoyl}methylamino)ethyl]piperidin-4-yl Ester A solid mixture of biphenyl-2-ylcarbamic acid 1-[2-({3-[2-(4-hydroxybenzylamino)ethylcarbamoyl]benzoyl}methylamino)ethyl]piperidin-4-yl ester (75 mg amorphous freebase; prepared as described in Example 1) and crystalline naphthalene-1,5-disulfonic acid (20.3 mg) was prepared in a 15 mL vial. The solids were dissolved by adding 2.5 mL of EtOH and heating to 40° C. for 5 minutes. Crystallization was induced by adding 2.5 mL of ACN and cooling to room temperature (approximately 22° C.) and leaving over night. Large birefringent well formed solid particles were obtained. These solids were analyzed by single crystal X-ray diffraction and found to be crystalline heminapadisylate ethanolate salt form of the parent ester.

Example 5

Crystalline Heminapadisylate Salt of Biphenyl-2-ylcarbamic Acid 1-[2-({3-[2-(4-Hydroxybenzylamino)ethylcarbamoyl]benzoyl}methylamino)ethyl]piperidin-4-yl Ester Crystalline heminapadisylate methanolate, prepared as described in Example 3, was converted to the desolvated crystal form of the ester by the following procedure: The filter cake was dried in an oven at 50° C., with a purging nitrogen flow, overnight, then at 40° C. over 3 days under vacuum. 19.75 g of the heminapadisylate salt was obtained as a white crystalline solid (84% yield freebase equivalent; 99.2% purity).

Alternately, the desolvated crystal form was prepared by heating the crystalline heminapadisylate methanolate form in a vacuum oven at 100° C., with a purging nitrogen flow for 4 hours (98.8% purity).

Alternately, the desolvated crystal form was prepared by reslurrying the crystalline heminapadisylate methanolate form in an excess of ACN (approximately 1-5% solids concentration) at 22° C. for two to four days (98.9% purity).

Example 6

Crystalline Freebase Biphenyl-2-ylcarbamic Acid 1-[2-({3-[2-(4-Hydroxybenzylamino)ethylcarbamoyl]benzoyl}methylamino)ethyl]piperidin-4-yl Ester (Form I)

Biphenyl-2-ylcarbamic acid 1-[2-({3-[2-(4-hydroxybenzylamino)ethylcarbamoyl]benzoyl}methylamino)ethyl]piperidin-4-yl ester (20 g amorphous freebase; prepared as described in Example 1) was dissolved in 200 mL of EtOAc and 60 mL of IPA room temperature. The solution was washed with water 2×100 mL. The organic phase was dried over MgSO4 then filtered. A small amount of crystals (90 mg; 97.5% purity) formed after filtration. The crystals were collected and dried under high vacuum before characterizations were performed.

Example 7

Crystalline Freebase Biphenyl-2-ylcarbamic Acid 1-[2-({3-[2-(4-Hydroxybenzylamino)ethylcarbamoyl]benzoyl}methylamino)ethyl]piperidin-4-yl Ester (Form II)

A 200 mg/mL solution was prepared by dissolving 50 mg of biphenyl-2-ylcarbamic acid 1-[2-({3-[2-(4-hydroxybenzylamino)ethylcarbamoyl]benzoyl}methylamino)ethyl]piperidin-4-yl ester (amorphous freebase; prepared as described in Example 1) in 0.25 mL of IPA at 22° C. in a glass HPLC vial. After two days, the vial was inspected by stereozoom microscope under polarized light. Birefringent particles were observed, indicating a crystalline morphology. After 7 days from initial dissolution, inspection of the vial found that crystals had continued to grow. The mother liquor was decanted and the crystals were washed with approximately 100-200 µL of 1:1 IPA:water. This material was confirmed to be crystalline by PXRD.

Figure 19:
FIG. 19 is a polarized light micrographic image of this crystalline freebase.

A larger batch was prepared for further characterization, by dissolving 200 mg of the amorphous freebase ester (prepared as described in Example 1) into 1.0 mL of IPA and 20 µL of water (2% vol/vol), at 22° C. Approximately 1-3 mg of seed crystals from the initial batch was added to the vial. The vial was left at 22° C. overnight, then inspected by stereozoom microscopy with crossed polarizing filters. Birefringent well formed crystals were observed covering the base of the vial; crystal size was typically 60-130 µm (see FIG. 19). These were further crystallized by cooling at 4° C., before isolation and characterization. HPLC analysis confirmed that the crystalline solid was consistent with the retention time of the parent compound (amorphous freebase ester) and the crystals had a purity of 98.6%, while the mother liquor purity was 96.7%. The amorphous feed material had a purity of 98.4%. Hence there was some purification achieved by crystallization of the freebase ester.

Example 8

Powder X-Ray Diffraction

Powder X-ray diffraction patterns shown in FIGS. 1, 10, 14 and 16 were obtained with a Rigaku diffractometer using Cu Kα radiation at 1.542 Å (30.0 kV, 15.0 mA) radiation. The analysis was performed with the goniometer running in continuous-scan mode of 3° per minute with a step size of 0.03° per point over a range of 2 to 45° in two-theta angle. Samples were prepared on quartz specimen holders as a thin layer of powdered material. The instrument was calibrated with a silicon metal standard. The PXRD patterns shown in FIG. 5 and FIG. 20 were obtained with a Thermo ARL X-Ray Diffractometer Model X'TRA (Thermo ARL SA, Switzerland) using Cu Kα radiation at 1.542 Å (45 kV, 40 mA) with a Si(Li) solid-state detector. The analysis was typically performed at a scan rate of 2° per minute with a step size of 0.03° per point over a range of 2 to 30° in two-theta angle. Samples were gently packed into a custom small-volume insert designed to fit into the instrument top-loading sample cup for analysis. The instrument calibration to within ±0.02° two-theta angle was verified weekly by comparison with a silicon metal standard.

The PXRD patterns for the compounds synthesized herein showed the materials to be crystalline. A representative PXRD pattern for a sample of the crystalline hemiedisylate salt of Example 2 is shown in FIG. 1. A representative PXRD pattern for a sample of the crystalline heminapadisylate methanolate of Example 3 is shown in FIG. 5A. A representative PXRD pattern for a sample of the heminapadisylate ethanolate of Example 4 is shown in FIG. 5B. A representative PXRD pattern for a sample of the crystalline heminapadisylate salt of Example 5 is shown in FIG. 10, as well as in FIG. 5C. A representative PXRD pattern for a sample of the crystalline freebase (Form I) of Example 6 is shown in FIG. 14. A representative PXRD pattern for a sample of the crystalline freebase (Form II) of Example 7 is shown in FIG. 16.

Example 9

Thermal Analysis

Differential scanning calorimetry (DSC) was performed using a TA Instruments Model Q-10 module with a Thermal Analyst controller. Data were collected and analyzed using TA Instruments Thermal Solutions software. A sample of about 1 mg was accurately weighed into an aluminum pan with lid. The sample was evaluated using a linear heating ramp of 5° C./min from ambient temperature to approximately 300° C. The DSC cell was purged with dry nitrogen during use.

The resulting DSC traces demonstrate that the crystalline salts, solvates and freebases of the invention have excellent thermal stability. A representative DSC trace for a sample of the crystalline hemiedisylate salt of Example 2 is shown in FIG. 2. Representative DSC traces for a sample of the crystalline heminapadisylate methanolate of Example 3 and a sample of the heminapadisylate ethanolate of Example 4, are presented in FIGS. 6A and 6B, respectively. A representative DSC trace for a sample of the crystalline heminapadisylate salt of Example 5 is shown in FIG. 11. A representative DSC trace for a sample of the crystalline freebase (Form I) of Example 6 is presented in FIG. 15. A representative DSC trace for a sample of the crystalline freebase (Form II) of Example 7 is shown in FIG. 17.

Thermogravimetric analysis (TGA) was performed using a TA Instruments Model Q-50 module equipped with high resolution capability. Data were collected and analyzed using TA Instruments Thermal Solutions software. A sample weighing about 2 mg was placed onto a platinum pan and scanned with a heating rate of 5° C./min from ambient temperature to 300° C. The balance and furnace chambers were purged with nitrogen flows during use.

The resulting TGA traces show that the crystalline salts, solvates and freebases of the invention lose a small amount of weight from room temperature to moderately elevated temperatures, which is consistent with the loss of residual moisture or solvent. A representative TGA trace for a crystalline hemiedisylate salt (prepared as described in Example 2) is shown in FIG. 2. A representative TGA trace for a crystalline heminapadisylate methanolate (prepared as described in Example 3) is presented in FIG. 7. A representative TGA trace for a heminapadisylate ethanolate (prepared as described in Example 4) is shown in FIG. 8. A representative TGA trace for a crystalline heminapadisylate salt (prepared as described in Example 5) is depicted in FIG. 11. A representative TGA trace for a crystalline freebase (Form I; prepared as described in Example 6) is shown in FIG. 15, and a representative TGA trace for a crystalline freebase (Form II; prepared as described in Example 7) is presented in FIG. 18.

Example 10

Dynamic Moisture Sorption Assessment

A dynamic moisture sorption (DMS) assessment (also known as a moisture sorption-desorption profile) was performed for samples of a crystalline hemiedisylate (prepared as described in Example 2) and a heminapadisylate (prepared as described in Example 5) salt using a VTI atmospheric microbalance, SGA-100 system (VTI Corp., Hialeah, Fla. 33016). A sample size of approximately 10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed stepwise to the next value (+/−5% RH) when the mass of the sample was stable to within 0.02% for 5 consecutive points.

Figure 3:
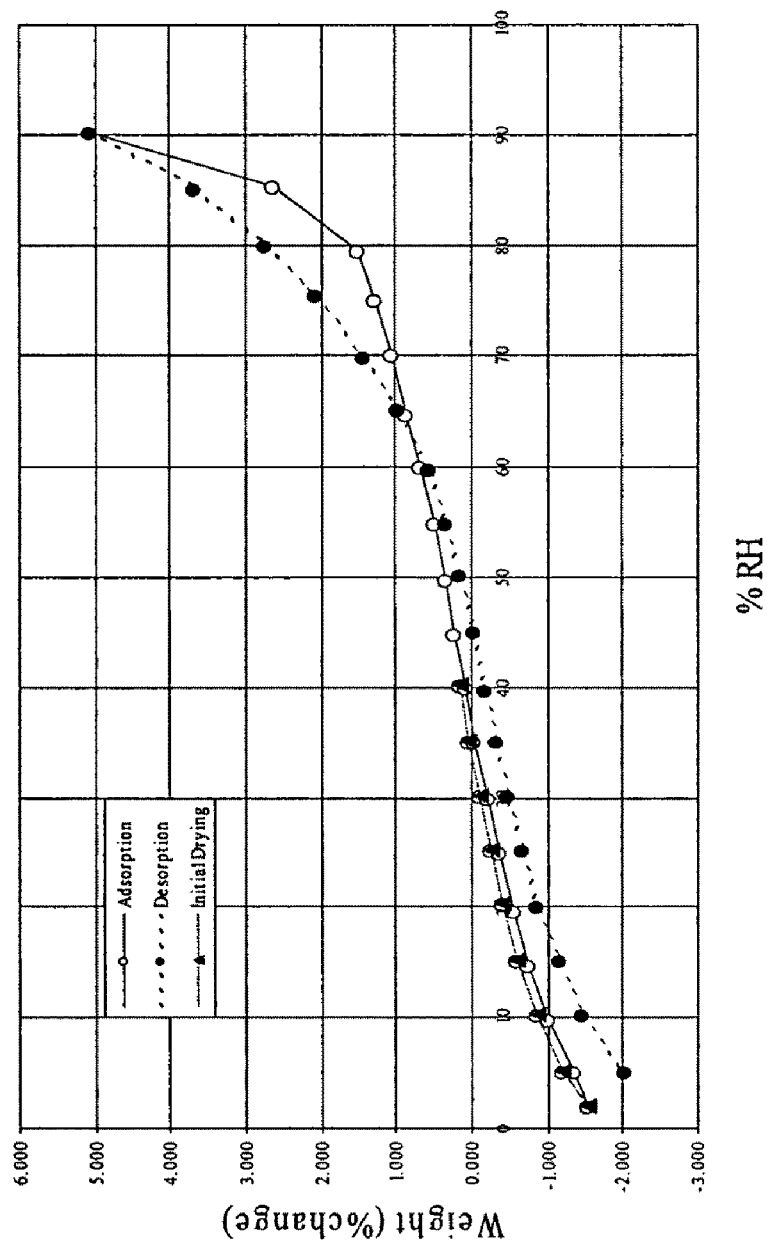
FIG. 3 shows a dynamic moisture sorption (DMS) trace for this crystalline salt.
Figure 4:
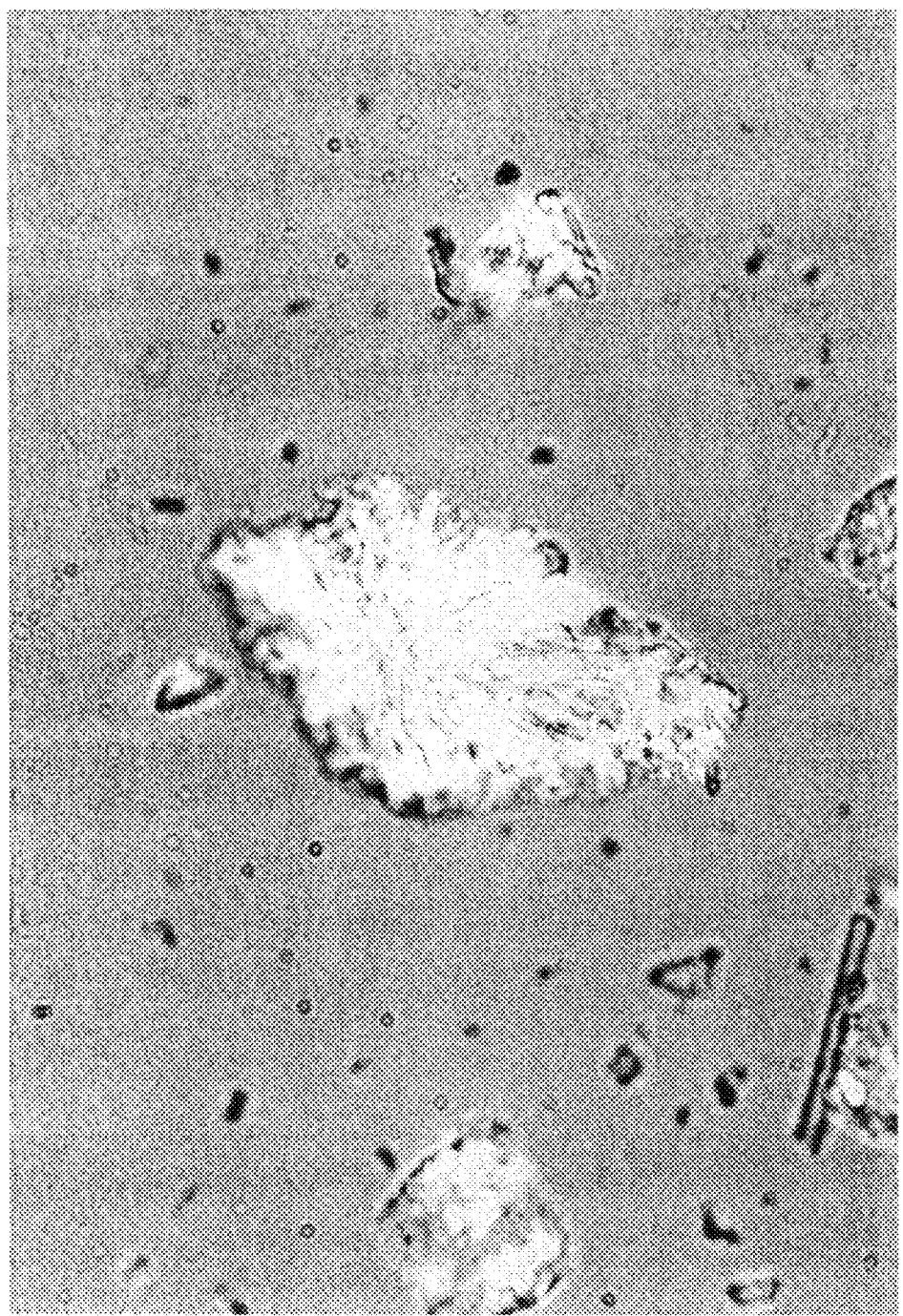
FIG. 4 is a polarized light micrographic image of this crystalline salt.

A representative DMS trace for a sample of the crystalline hemiedisylate salt showed a reversible sorption/desorption profile with a moderate level of hygroscopicity, with less than about 4% weight gain when exposed to up to 90% RH, as shown in FIG. 3.

Figure 12:
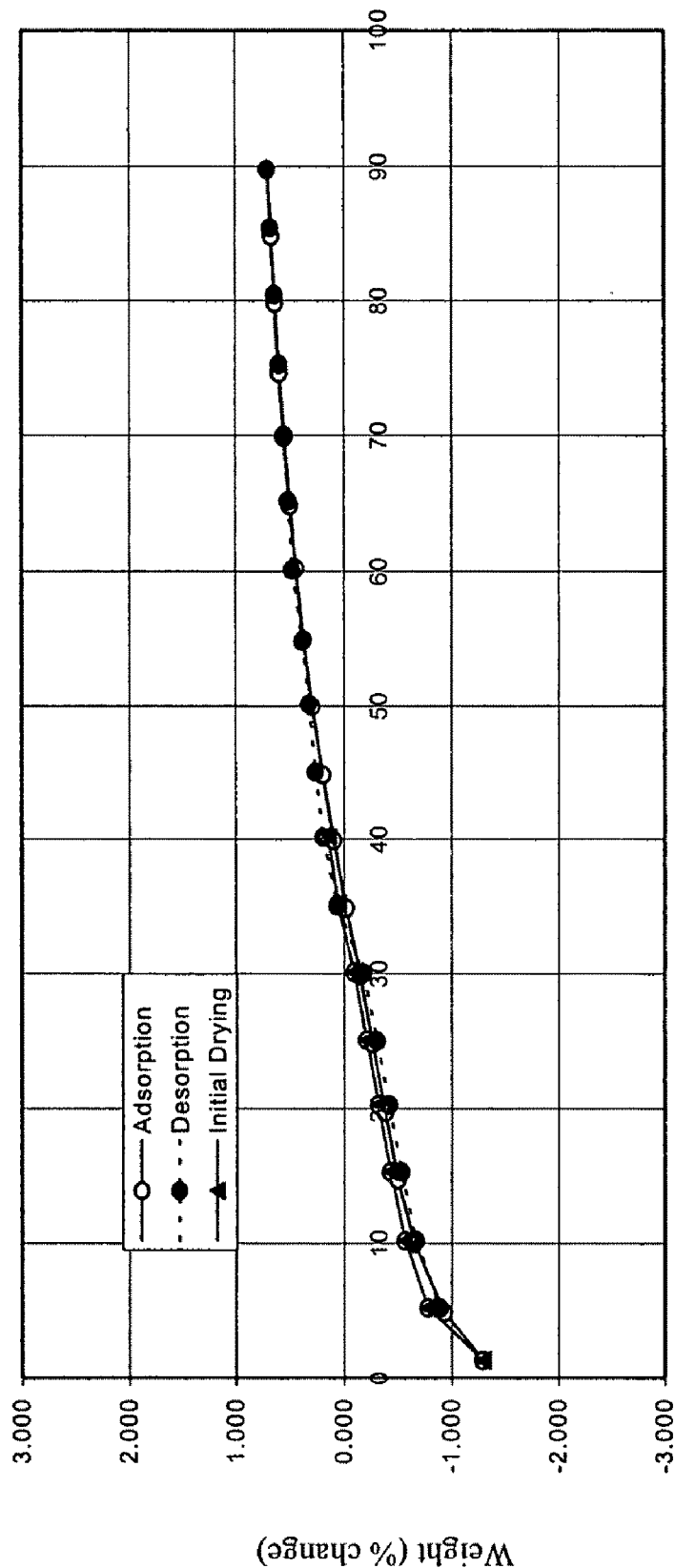
Figure 13:
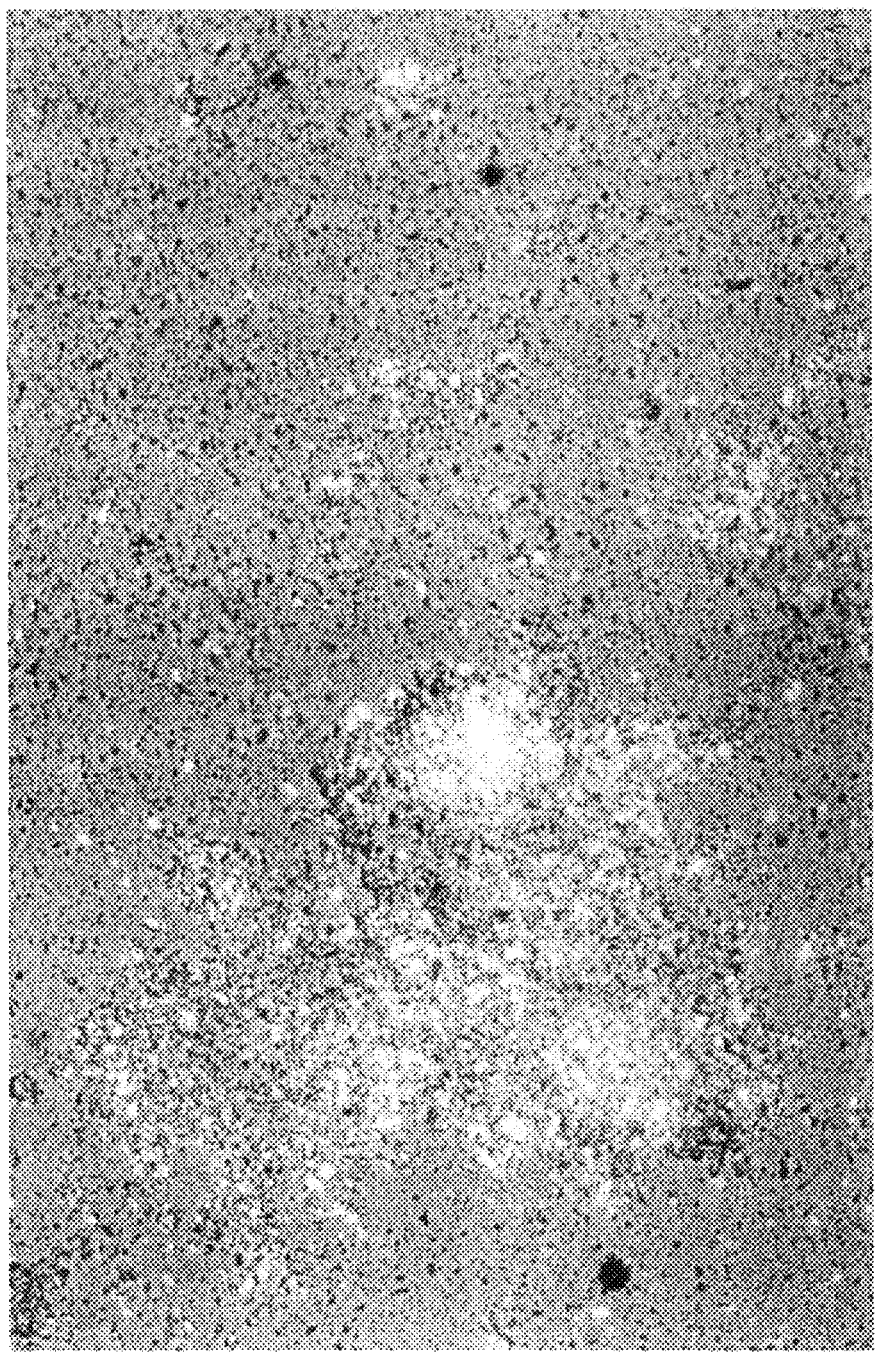

A representative DMS trace for a sample of the crystalline heminapadisylate salt showed a reversible sorption/desorption profile with a low level of hygroscopicity, with less than about 2% weight gain when exposed to up to 90% RH, as shown in FIG. 12.

DMS assessment was also performed for samples of the crystalline diacetate, monooxalate and dipropionate salts described in Example 1. A representative DMS trace for the crystalline diacetate salt showed a reversible sorption/desorption profile with a less than about 18% weight gain when exposed to up to 90% RH. A representative DMS trace for the crystalline monooxalate salt showed a reversible sorption/desorption profile with less than about 14% weight gain when exposed to up to 90% RH. A representative DMS trace for a crystalline dipropionate salt showed a reversible sorption/desorption profile with less than about 11% weight gain when exposed to up to 90% RH.

Based upon this date, the crystalline hemiedisylate and heminapadisylate salts of the present invention have reversible sorption/desorption profiles with low hygroscopicity and have acceptable weight gains when exposed to a broad humidity range. This demonstrates that the crystalline hemiedisylate and heminapadisylate salts possess an acceptable hygroscopicity and are not deliquescent, thus making them particularly well suited for use in formulations to be administered by inhalation, in particular by dry powder inhalers.

Example 11

Elemental/Ion Analysis

Elemental percentages were determined by combustion analysis using a Flash EA 1112 Elemental Analyzer (CE Elantech, Lakewood, N.J.). The elemental percentages for a sample of the crystalline hemiedisylate salt of Example 2 were determined to be 8.8% nitrogen and 4.62% sulfur (calculated values: 9.4% nitrogen and 4.3%% sulfur). Elemental percentages for a sample of the crystalline heminapadisylate salt of Example 5 were determined to be 8.4% nitrogen and 3.7% sulfur (calculated values: 8.8% nitrogen and 4.0% sulfur). In addition, ion analysis of the crystalline heminapadisylate salt determined 18.0% w/w napadisylate (calculated value: 18.14% w/w).

Example 12

X-Ray Structure Analysis

A chunk crystal of a heminapadisylate ethanolate, produced as described in Example 4 was mounted on a glass fiber. X-ray structure data was obtained using a Bruker SMART 6K CCD-ray area detector with window diameter of 13.5 cm., controlled by SMART version 5.630 software (Bruker, 2003) using Cu Kα radiation. The sample to detector distance was 5.039 cm. Data was collected at a temperature of $-153\pm1°$ C. and was analyzed using SHELXS version 6.14 (Bruker, 2003) software. The following lattice parameters were derived: unit cell was primitive triclinic with dimensions a=8.9384 Å, b=9.9389 Å, c=24.8153 Å,; α=95.1580°, β=90.8130°, and γ=105.5160°; the space group was P-1; and the calculated density was 1.32 g/cm$^3$.

Figure 20:
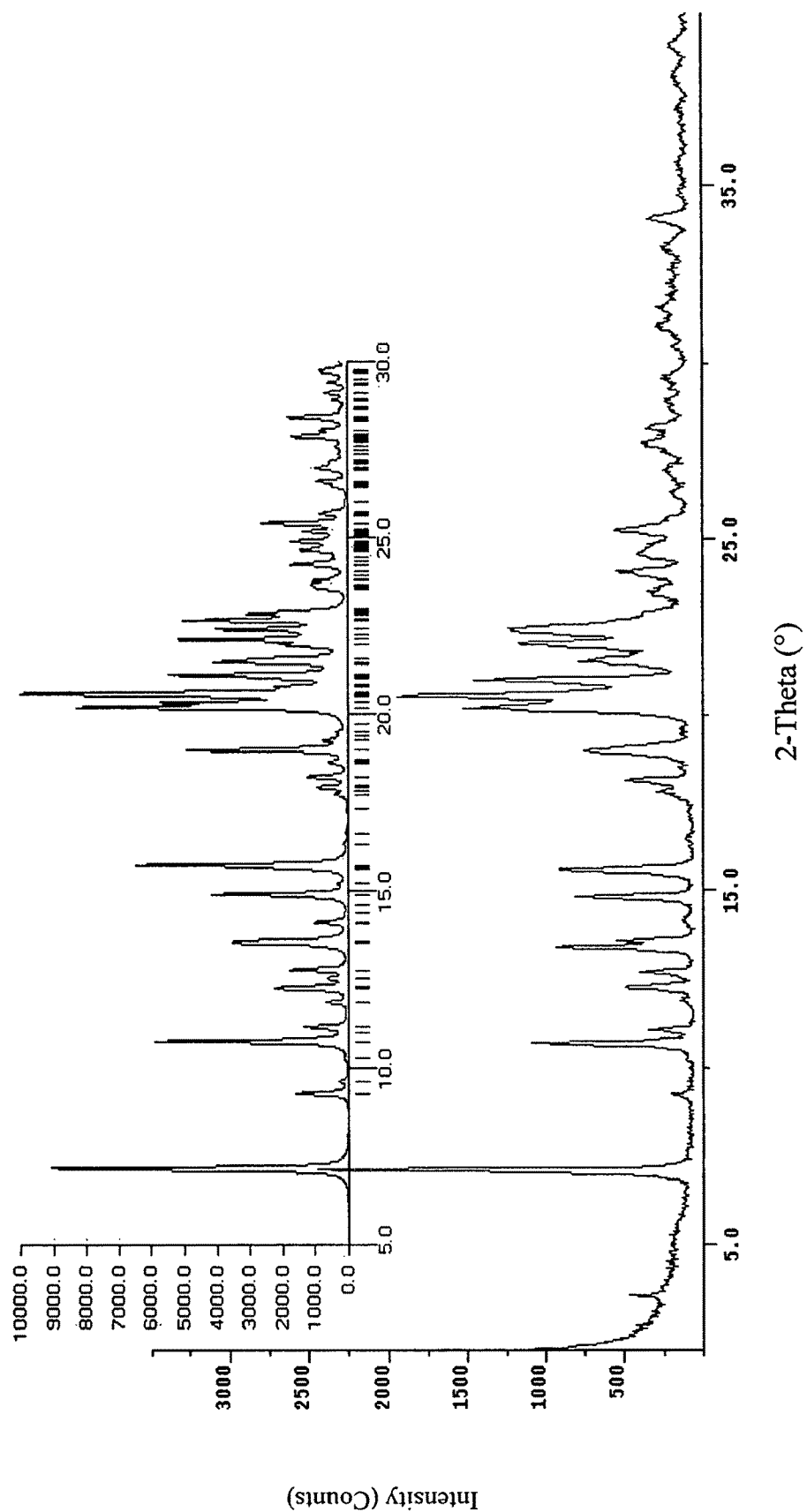
FIG. 20 depicts an overlay of the predicted and experimental PXRD patterns for a crystalline heminapadisylate ethanolate of the compound of formula I.

FIG. 20 depicts an overlay of the PXRD pattern predicted from this structure analysis with the experimental PXRD data, showing highly consistent diffraction peak positions for this crystalline heminapadisylate ethanolate.

Example 13

Micronization

A 12.1 g sample of a crystalline heminapadisylate salt (prepared as described in Example 5) was micronized to give 9.3 g of a free-flowing white powder (77% recovery). Pre-micronization, the crystalline heminapadisylate had a purity of 99.2% as determined by HPLC area percentage. The purity of the micronized material was the same. The water content of the pre-micronized material was 2.61 wt %, and the water content of the micronized material was 2.98 wt %. The particle size distribution was as follows:

|  | Pre-Micronization | Post-Micronization |
|---|---|---|
| D(v, 0.9) | 41.1 μm | 3.3 μm |
| D(v, 0.5) | 6.0 μm | 1.1 μm |
| D(v, 0.1) | 0.4 μm | 0.3 μm |

No significant changes were observed in the powder x-ray diffraction pattern, TGA, DSC, DMS, chemical purity, chiral purity and moisture content for the micronized material compared to the unmicronized material. For example, the crystalline salt showed a 0.46% weight gain in the humidity range of 40-75% RH, while the micronized material showed a 0.56% weight gain in this range.

Example 14

Solid State Stability Assessment

Samples of a crystalline heminapadisylate salt (prepared as described in Example 5), about 200 mg each, were stored in multiple 3 mL borosilicate vials at 40° C. and 75% RH. The samples were as follows, where micronization was done as described in example 13: un-micronized salt (neat), micronized salt (neat), micronized salt with 0.3% lactose (w/w freebase equivalents), and micronized salt with 3% lactose (w/w freebase equivalents).

At specific intervals, the entire contents of a representative vial was analyzed by HPLC. The following exemplifies one such method: Column: Agilent Zorbox SB-C18, 4.6×250 mm, 5 μm; Mobile Phase A: 98% water, 2% ACN, 0.1% TFA; Mobile Phase B: 10% water, 90% ACN; 0.1% TFA; Flow rate: 1 mL/min; Injection Volume: 20 μL; Detector: 220 nm; Gradient-Time in minutes (% Mobile Phase B): 0.0 (10); 4.00 (20); 26.00 (28); 34.40 (100); 38.40 (100); 38.50 (10); and 45.00 (10). Samples were prepared as 10 mg/mL stock solutions in 10-50% ACN in H$_2$O, depending on the solubility. These stock solutions were diluted to 1 mg/mL in 10% ACN for injection onto the HPLC.

After about 1 month of storage, all samples showed no observable physical changes, no detectable chemical degradation (i.e., less than about 0.5% degradation for the neat salt, about 3% degradation for the 0.3% lactose blend, and about 0.6% degradation for the 3% lactose blend).

Example 15

Inhalation Solution Stability

A solution was prepared with 0.2 mg/mL freebase equivalents (using a crystalline heminapadisylate salt prepared as described in Example 5) in 10 mM citrate buffered normal saline, pH 4.5. Less than 0.5% degradation was observed after storage for one month at 40° C./75% RH.

Assay 1

Radioligand Binding Assay

Membrane Preparation from Cells Expressing hM$_1$, hM$_2$, hM$_3$ and hM$_4$ Muscarinic Receptor Subtypes CHO cell lines stably expressing cloned human hM$_1$, hM$_2$, hM$_3$ and hM$_4$ muscarinic receptor subtypes, respectively, were grown to near confluency in medium consisting of HAM's F-12 supplemented with 10% FBS and 250 μg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared $hM_5$ receptor membranes were purchased directly from PerkinElmer and stored at −80° C. until use.

Radioligand Binding Assay on Muscarinic Receptor Subtypes $hM_1$, $hM_2$, $hM_3$, $hM_4$ and $hM_5$ Radioligand binding assays were performed in 96-well microtiter plates in a total assay volume of 100 μL. CHO cell membranes stably expressing either the $hM_1$, $hM_2$, $hM_3$, $hM_4$ or $hM_5$ muscarinic subtype were diluted in assay buffer to the following specific target protein concentrations (μg/well): 10 μg for $hM_1$, 10-15 μg for $hM_2$, 10-20 μg for $hM_3$, 10-20 μg for $hM_4$, and 10-12 μg for $hM_5$. The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were then air dried, and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. *Biochemical Pharmacology* 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. The compound of formula I was found to have a $K_i$ value of less than about 5 nM for the $M_3$ muscarinic receptor subtype when tested in this or a similar assay.

Assay 2

Muscarinic Receptor Functional Potency Assays

Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K1 cells expressing the $hM_2$ receptor. cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mLs dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6 \times 10^6$-$2.8 \times 10^6$ cells/mL.

The test compound was initially dissolved to a concentration of 400 μM in dilution buffer (+ supplemented with 1 mg/mL BSA (0.1%)), and then serially diluted with dilution buffer to final molar concentrations ranging from 100 μM to 0.1 nM. Oxotremorine was diluted in a similar manner.

To measure oxotremorine inhibition of AC activity, 25 μL forskolin (25 μM final concentration diluted in dPBS), 25 μL diluted oxotremorine, and 50 μL cells were added to agonist assay wells. To measure the ability of a test compound to block oxotremorine-inhibited AC activity, 25 μL forskolin and oxotremorine (25 μM and 5 μM final concentrations, respectively, diluted in dPBS), 25 μL diluted test compound, and 50 μL cells were added to remaining assay wells. Reactions were incubated for 10 minutes at 37° C. and stopped by addition of 100 μL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively. The $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher functional activity at the receptor tested. The compound of formula I was found to have a $K_i$ value of less than about 5 nM for blockade of oxotremorine-inhibition of forskolin-mediated cAMP accumulation in CHO-K1 cells expressing the $hM_2$ receptor, when tested in this or a similar assay.

Blockade of Agonist-Mediated [$^{35}$S]GTPγS Binding

In a second functional assay, the functional potency of test compounds can be determined by measuring the ability of the compounds to block oxotremorine-stimulated [$^{35}$S]GTPγS binding in CHO-K1 cells expressing the $hM_2$ receptor.

At the time of use, frozen membranes were thawed and then diluted in assay buffer with a final target tissue concentration of 5-10 μg protein per well. The membranes were briefly homogenized using a Polytron PT-2100 tissue disrupter and then added to the assay plates. The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 μL of assay buffer with [$^{35}$S]GTPγS (0.4 nM), 25 μL of oxotremorine (EC90) and GDP (3 μM), 25 μL of diluted test compound and 25 μL CHO cell membranes expressing the $hM_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. The compound of formula I was found to have a $K_i$ value of less than about 10 nM for blockade of oxotremorine-stimulated [$^{35}$S]GTPγS binding in CHO-K1 cells expressing the $hM_2$ receptor, when tested in this or a similar assay.

Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event was measured in real time by the FLIPR, which detected the change in fluorescence from a monolayer of cells cloned with human $M_1$ and $M_3$, and chimpanzee $M_5$ receptors. Antagonist potency was determined by the ability of antagonists to inhibit agonist-mediated increases in intracellular calcium.

For FLIPR calcium stimulation assays, CHO cells stably expressing the $hM_1$, $hM_3$ and $cM_5$ receptors were seeded into 96-well FLIPR plates the night before the assay was done. Seeded cells were washed twice by Cellwash (MTX Labsystems, Inc.) with FLIPR buffer (10 mM HEPES, pH 7.4, 2 mM calcium chloride, 2.5 mM probenecid in HBSS without calcium and magnesium) to remove growth media and leaving 50 μL/well of FLIPR buffer. The cells were then incubated with 50 μL/well of 4 μM FLUO-4AM (a 2× solution was made) for 40 minutes at 37° C., 5% carbon dioxide. Following the dye incubation period, cells were washed two times with FLIPR buffer, leaving a final volume of 50 μL/well.

To determine antagonist potency, the dose-dependent stimulation of intracellular $Ca^{2+}$ release for oxotremorine was first determined so that antagonist potency can later be measured against oxotremorine stimulation at an $EC_{90}$ concentration. Cells were first incubated with compound dilution buffer for 20 minutes, followed by agonist addition, which is performed by the FLIPR. An $EC_{90}$ value for oxotremorine was generated according to the method detailed in the FLIPR measurement and data reduction section below, in conjunction with the formula $EC_F=((F/100-F)^{\wedge}1/H)*EC_{50}$. An oxotremorine concentration of $3 \times EC_F$ is prepared in stimulation plates such that an $EC_{90}$ concentration of oxotremorine was added to each well in the antagonist inhibition assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change. The change of fluorescence was expressed as maximum fluorescence minus baseline fluorescence for each well. The raw data was analyzed against the logarithm of drug concentration by nonlinear regression with GraphPad Prism (GraphPad Software, Inc., San Diego, Calif.) using the built-in model for sigmoidal dose-response. Antagonist $K_i$ values were determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. The compound of formula I was found to have a $K_i$ value of less than about 10 nM for blockade of agonist-mediated calcium release in CHO cells stably expressing the $hM_3$ receptor, when tested in this or a similar assay.

Assay 3

Determination of Duration of Bronchoprotection in Guinea Pig Model of Acetylcholine-Induced Bronchoconstriction This in vivo assay is used to assess the bronchoprotective effects of test compounds exhibiting muscarinic receptor antagonist activity. Groups of six male guinea pigs (Duncan-Hartley (HsdPoc:DH) Harlan, Madison, Wis.) weighing between 250 and 350 g are individually identified by cage cards. Throughout the study, animals are allowed access to food and water ad libitum.

Test compounds are administered via inhalation over 10 minutes in a whole-body exposure dosing chamber (R&S Molds, San Carlos, Calif.). The dosing chambers are arranged so that an aerosol was simultaneously delivered to 6 individual chambers from a central manifold. Guinea pigs are exposed to an aerosol of a test compound or vehicle (WFI). These aerosols are generated from aqueous solutions using an LC Star Nebulizer Set (Model 22F51, PARI Respiratory Equipment, Inc. Midlothian, Va.) driven by a mixture of gases ($CO_2=5\%$, $O_2=21\%$ and $N_2=74\%$) at a pressure of 22 psi. The gas flow through the nebulizer at this operating pressure is approximately 3 L/minute. The generated aerosols are driven into the chambers by positive pressure. No dilution air is used during the delivery of aerosolized solutions. During the 10 minute nebulization, approximately 1.8 mL of solution is nebulized. This is measured gravimetrically by comparing pre-and post-nebulization weights of the filled nebulizer.

The bronchoprotective effects of test compounds administered via inhalation are evaluated using whole body plethysmography at 1.5, 24, 48 and 72 hours post-dose.

Forty-five minutes prior to the start of the pulmonary evaluation, each guinea pig is anesthetized with an intramuscular injection of ketamine (43.75 mg/kg), xylazine (3.50 mg/kg) and acepromazine (1.05 mg/kg). After the surgical site is shaved and cleaned with 70% alcohol, a 2-3 cm midline incision of the ventral aspect of the neck was made. Then, the jugular vein is isolated and cannulated with a saline-filled polyethylene catheter (PE-50, Becton Dickinson, Sparks, Md.) to allow for intravenous infusions of ACh (Sigma-Aldrich, St. Louis, Mo.) in saline. The trachea is then dissected free and cannulated with a 14G teflon tube (#NE-014, Small Parts, Miami Lakes, Fla.). If required, anesthesia is maintained by additional intramuscular injections of the aforementioned anesthetic mixture. The depth of anesthesia is monitored and adjusted if the animal responds to pinching of its paw or if the respiration rate is greater than 100 breaths/minute.

Once the cannulations are complete, the animal is placed into a plethysmograph (#PLY3114, Buxco Electronics, Inc., Sharon, Conn.) and an esophageal pressure cannula (PE-160, Becton Dickinson, Sparks, Md.) is inserted to measure pulmonary driving pressure (pressure). The teflon tracheal tube is attached to the opening of the plethysmograph to allow the guinea pig to breathe room air from outside the chamber. The chamber is then sealed. A heating lamp is used to maintain body temperature and the guinea pig's lungs are inflated 3 times with 4 mL of air using a 10 mL calibration syringe (#5520 Series, Hans Rudolph, Kansas City, Mo.) to ensure that the lower airways do not collapse and that the animal does not suffer from hyperventilation.

Once it is determined that baseline values are within the range 0.3-0.9 mL/cm $H_2O$ for compliance and within the range 0.1-0.199 cm $H_2O$/mL per second for resistance, the pulmonary evaluation is initiated. A Buxco pulmonary measurement computer program enables the collection and derivation of pulmonary values.

Starting this program initiates the experimental protocol and data collection. The changes in volume over time that occur within the plethysmograph with each breath are measured via a Buxco pressure transducer. By integrating this signal over time, a measurement of flow is calculated for each breath. This signal, together with the pulmonary driving pressure changes, which are collected using a Sensym pressure transducer (#TRD4100), is connected via a Buxco (MAX 2270) preamplifier to a data collection interface (#'s SFT3400 and SFT3813). All other pulmonary parameters are derived from these two inputs.

Baseline values are collected for 5 minutes, after which time the guinea pigs are challenged with ACh. ACh (0.1 mg/mL) is infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. If resistance or compliance has not returned to baseline values at 3 minutes following each ACh dose, the guinea pig's lungs are inflated 3 times with 4 mL of air from a 10 mL calibration syringe. Recorded pulmonary parameters includes respiration frequency (breaths/minute), compliance (mL/cm $H_2O$) and pulmonary resistance (cm $H_2O$/mL per second). Once the pulmonary function measurements are completed at minute 35 of this protocol, the guinea pig is removed from the plethysmograph and euthanized by carbon dioxide asphyxiation.

The data are evaluated in one or both of the following ways:

(a) Pulmonary resistance ($R_L$, cm $H_2O$/mL per second) is calculated from the ratio of "change in pressure" to "the change in flow." The $R_L$ response to ACh (60 μg/min, IH) is computed for the vehicle and the test compound groups. The mean ACh response in vehicle-treated animals, at each pre-treatment time, is calculated and used to compute % inhibition of ACh response, at the corresponding pre-treatment time, at each test compound dose. Inhibition dose-response curves for '$R_L$' are fitted with a four parameter logistic equation using GraphPad Prism, version 3.00 for Windows (GraphPad Software, San Diego, Calif.) to estimate bronchoprotective $ID_{50}$ (dose required to inhibit the ACh (60 μg/min) bronchoconstrictor response by 50%). The equation used is as follows:

$$Y = \text{Min} + (\text{Max} - \text{Min})/(1 + 10^{((\log ID50 - X)*Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of ACh or histamine needed to cause a doubling of the baseline pulmonary resistance, is calculated using the pulmonary resistance values derived from the flow and the pressure over a range of ACh or histamine challenges using the following equation (which is derived from a equation used to calculate $PC_{20}$ values described in American Thoracic Society. Guidelines for methacholine and exercise challenge testing—1999. *Am J Respir Crit Care Med*. 161: 309-329 (2000)):

$$PD_2 = \text{antilog}\left[\log C_1 + \frac{(\log C_2 - \log C_1)(2R_0 - R_1)}{R_2 - R_1}\right]$$

where: $C_1$ is the concentration of ACh or histamine preceding $C_2$; $C_2$ is the concentration of ACh or histamine resulting in at least a 2-fold increase in pulmonary resistance ($R_L$); $R_0$ is the baseline $R_L$ value; $R_1$ is the $R_L$ value after $C_1$; and $R_2$ is the $R_L$ value after $C_2$. An efficacious dose is defined as a dose that limits the bronchorestriction response to a 50 μg/mL dose of ACh to a doubling of the baseline pulmonary resistance ($PD_{2(50)}$).

Statistical analysis of the data is performed using a two-tailed Students t-test. A P-value<0.05 is considered significant. Generally, test compounds having a $PD_{2(50)}$ less than about 200 μg/mL for ACh-induced bronchoconstriction at 1.5 hours post-dose in this assay are preferred. The compound of formula I is expected to have a $PD_{2(50)}$ less than about 200 μg/mL for ACh-induced bronchoconstriction at 1.5 hours post-dose, when tested in this or a similar assay.

Assay 4

Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (IH) over a 10 minute time period in a pie shaped dosing chamber (R&S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment.

Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, SC) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol* 24:243-254 (1996).

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The following equation is used:

$$Y = \text{Min} + (\text{Max} - \text{Min})/(1 + 10^{((\log ID_{50} - X) \cdot Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ is used to compute the apparent lung selectivity index of the test compound. Generally, compounds having an apparent lung selectivity index greater than about 5 are preferred. The compound of formula I is expected to have an apparent lung-selectivity index greater than about 5, when tested in this or a similar assay.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g are used in these studies. Under isoflurane anesthesia (to effect), animals are instrumented with common carotid artery and jugular vein catheters (PE-50 tubing). The catheters are exteriorized utilizing a subcutaneous tunnel to the subscapular area. All surgical incisions are sutured with 4-0 Ethicon Silk and the catheters locked with heparin (1000 units/mL). Each animal is administered saline (3 mL, SC) at the end of surgery as well as buprenorphine (0.05 mg/kg, IM). Animals are allowed to recover on a heating pad before being returned to their holding rooms.

Approximately 18 to 20 hours following surgery, the animals are weighed and the carotid artery catheter on each animal is connected to a transducer for recording arterial pressure. Arterial pressure and heart rate are recorded using a Biopac MP-100 Acquisition System. Animals are allowed to acclimate and stabilize for a period of 20 minutes.

Each animal is challenged with MCh (0.3 mg/kg, IV) administered through the jugular venous line and the cardiovascular response is monitored for 10 minutes. The animals are then placed into the whole body dosing chamber, which is connected to a nebulizer containing the test compound or vehicle solution. The solution is nebulized for 10 minutes using a gas mixture of breathable air and 5% carbon dioxide with a flow rate of 3 liters/minute. The animals are then removed from the whole body chamber and returned to their respective cages. At 1.5 and 24 hours post-dosing, the animals are re-challenged with MCh (0.3 mg/kg, IV) and the hemodynamic response is determined. Thereafter, the animals are euthanized with sodium pentobarbital (150 mg/kg, IV).

MCh produces a decrease in mean arterial pressure (MAP) and decrease in heart rate (bradycardia). The peak decrease, from baseline, in MAP (depressor responses) is measured for each MCh challenge (before and after IH dosing). The effects of treatment on the MCh responses are expressed as % inhibition (mean+/−SEM) of the control depressor responses. Two-way ANOVA with the appropriate post-hoc test is used to test the effects of treatment and pre-treatment time. The depressor responses to MCh are expected to be relatively unchanged at 1.5 and 24 hours after inhalation dosing with vehicle.

The ratio of the anti-depressor $ID_{50}$ to bronchoprotective $ID_{50}$ is used to compute apparent lung-selectivity of the test compound. Generally, compounds having an apparent lung-selectivity index greater than 5 are preferred. It is expected that the compound of formula I will exhibit an apparent lung-selectivity index greater than 5, when tested in this or a similar assay.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A crystalline hemiedisylate salt of biphenyl-2-ylcarbamic acid 1-[2-({3-[2-(4-hydroxybenzylamino)ethylcarbamoyl]benzoyl} methylamino)ethyl] piperidin-4-yl ester, characterized by a powder x-ray diffraction pattern comprising diffraction peaks at 2θ values of 8.14±0.20, 9.90±0.20, 12.57±0.20, 13.92±0.20, 16.32±0.20, 17.46±0.20, 19.26±0.20, 21.21±0.20, 22.42±0.20, 23.16±0.20, 23.64±0.20, 25.08±0.20, 27.00±0.20, 29.55±0.20, and 30.84±0.20.

2. The compound of claim 1, characterized by a differential scanning calorimetry trace which shows a maximum endothermic heat flow at about 150 ° C.

3. The compound of claim 1, characterized by a powder x-ray diffraction pattern in which the peak positions are substantially in accordance with the peak positions of the pattern shown in FIG. 1, and a differential scanning calorimetry trace substantially in accordance with that shown in FIG. 2.

4. A pharmaceutical composition comprising a pharmaceutically acceptable carrier and a therapeutically effective amount of a compound of claim 1.

5. The composition of claim 4, which is formulated for administration by inhalation.

* * * * *